United States Patent [19]

Takaya et al.

[11] 4,254,260
[45] Mar. 3, 1981

[54] 3-SUBSTITUTED-7-SUBSTITUTED ALKANAMIDO-3-CEPHEM-4-CARBOXYLIC ACID COMPOUNDS

[75] Inventors: Takao Takaya, Sakai; Takashi Masugi, Toyonaka; Hisashi Takasugi, Osaka; Hiromu Kochi, Sakai, all of Japan

[73] Assignee: Fujisawa Pharmaceutical Co., Ltd., Osaka, Japan

[21] Appl. No.: 691,842

[22] Filed: Jun. 1, 1976

[30] Foreign Application Priority Data

Mar. 6, 1975 [GB] United Kingdom .............. 23992/75
Sep. 16, 1975 [GB] United Kingdom .............. 38108/75
Nov. 5, 1975 [GB] United Kingdom .............. 45968/75

[51] Int. Cl.³ .......................................... C07D 501/36
[52] U.S. Cl. ...................................... 544/27; 544/26; 424/246
[58] Field of Search ................ 260/243 C; 544/27, 26

[56] References Cited

U.S. PATENT DOCUMENTS

| | | | |
|---|---|---|---|
| 3,516,997 | 6/1970 | Takano et al. | 260/243 C |
| 3,821,207 | 6/1974 | Chow et al. | 260/243 C |
| 3,891,635 | 6/1975 | Henninger et al. | 260/243 C |
| 3,907,787 | 9/1975 | Teller et al. | 260/243 C |
| 4,080,498 | 3/1978 | Numata et al. | 544/27 |

*Primary Examiner*—Nicholas S. Rizzo
*Attorney, Agent, or Firm*—Dayton R. Stemple, Jr.

[57] ABSTRACT

3-Substituted-7-substituted alkanamido-3-cephem-4-carboxylic acid compounds and pharmaceutically acceptable salts thereof which have antimicrobial activities, processes for the preparation thereof, pharmaceutical compositions comprising the same, and methods of using the same therapeutically in the treatment of infections.

8 Claims, No Drawings

1

3-SUBSTITUTED-7-SUBSTITUTED ALKANAMIDO-3-CEPHEM-4-CARBOXYLIC ACID COMPOUNDS

The present invention relates to new 3-substituted-7-substituted alkanamido-3-cephem-4-carboxylic acid compounds and pharmaceutically acceptable salts thereof. More particularly, it relates to new 3-substituted-7-substituted alkanamido-3-cephem-4-carboxylic acid compounds and pharmaceutically acceptable salts thereof which have antimicrobial activities and to processes for the preparation thereof, to pharmaceutical composition comprising the same, and to a method of using the same therapeutically in the treatment of infections.

Accordingly, it is one object to the present invention to provide the antimicrobially active 3-substituted-7-substituted alkanamido-3-cephem-4-carboxylic acid compounds and pharmaceutically acceptable salts thereof, which are active against a number of pathogenic microorganisms.

Another object of the present invention is to provide processes for the preparation of 3-substituted-7-substituted alkanamido-3-cephem-4-carboxylic acid compounds and pharmaceutically acceptable salts thereof.

A further object of the present invention is to provide pharmaceutical composition comprising, as effective antimicrobial agents, said 3-substituted-7-substituted alkanamido-3-cephem-4-carboxylic acid compounds and pharmaceutically acceptable salts thereof.

Still further object of the present invention is to provide a method for the treatment of infectious disease caused by bacteria in human being and animals.

The object 3-substituted-7-substituted alkanamido-3-cephem-4-carboxylic acid compounds are novel and can be represented by the following general formula (I)

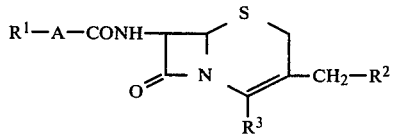

wherein
R$^1$ is a heterocyclic group of the formula:

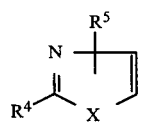

in which R$^4$ is amino or hydroxy, R$^5$ is hydrogen or lower alkyl and X; is —S—, —O—, imino or lower alkylimino,
R$^2$ is carbamoyloxy, lower alkanamido(lower)alkylthiadiazolylthio, lower alkenyltetrazolylthio or benzimidazolylthio,
R$^3$ is carboxy or protected carboxy and
A is lower alkylene; or
R$^1$ is a heterocyclic group selected from the groups consisting of:

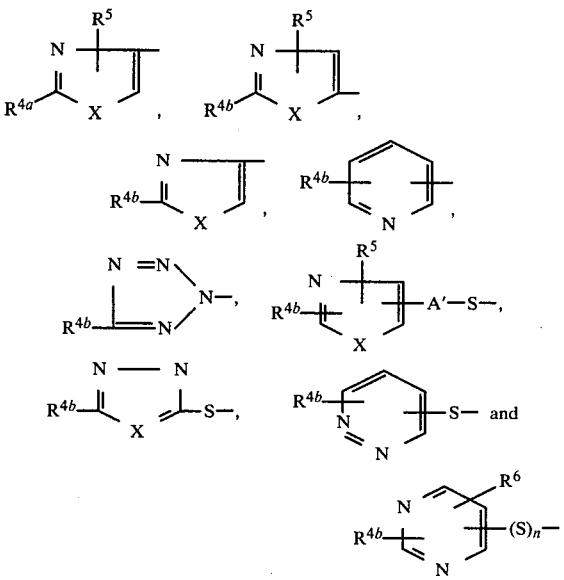

in which
R$^{4a}$ is halogen, halo(lower)alkanamido, lower alkanesulfonamido, arenesulfonamido, ureido, lower alkylureido, amino(lower)alkyl or protected amino(lower)alkyl, R$^{4b}$ is amino, hydroxy, halogen, protected amino, amino(lower)alkyl, protected amino(lower)alkyl or lower alkylamino,
R$^5$ is hydrogen or lower alkyl, R$^6$ is hydrogen, hydroxy or halogen, A' is a bond or lower alkylene, n is an integer of 0 or 1 and X is —S—, —O—, imino or lower alkylimino,
R$^2$ is acyloxy or a heterocyclic-thio group which may have suitable substituent(s),
R$^3$ is carboxy or protected carboxy and
A is lower alkylene.

According to the present invention, the 3-substituted-7-substituted alkanamido-3-cephem-4-carboxylic acid compounds (I) can be prepared by conventional various processes which are illustrated by the following scheme, in which the process comprising step (II) to (I) is a fundamental process and the others are alternative processes.

Process 1

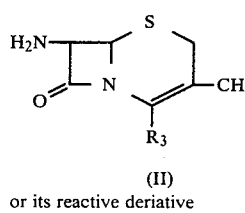
(II)
or its reactive deriative at the amino group or a

R$^1$—A—COOH (III)
or its reactive derivative at the carboxy group, and then optionally followed by elimination of the protective group of the amino →

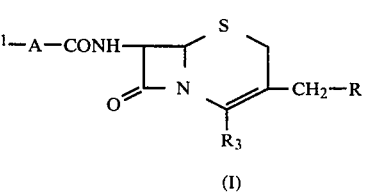
(I)

salt thereof

Process 2

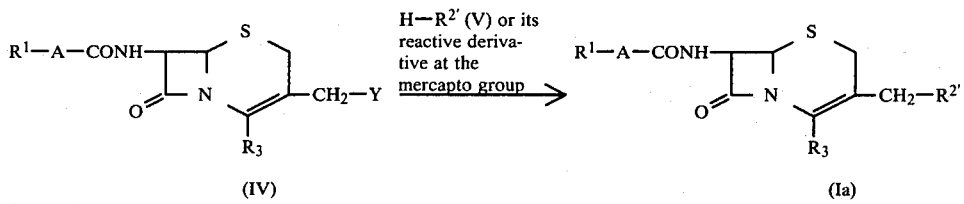

(IV) → (Ia)

Process 3

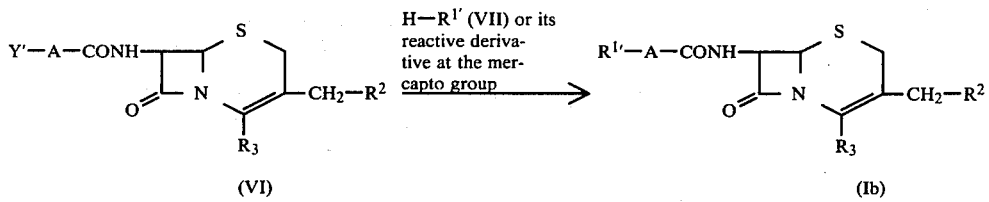

(VI) → (Ib)

Process 4

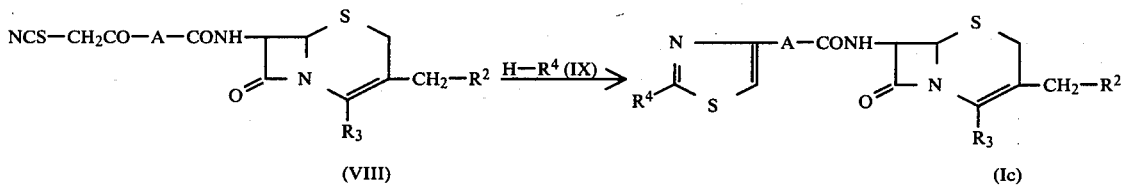

(VIII) → (Ic)

Process 5

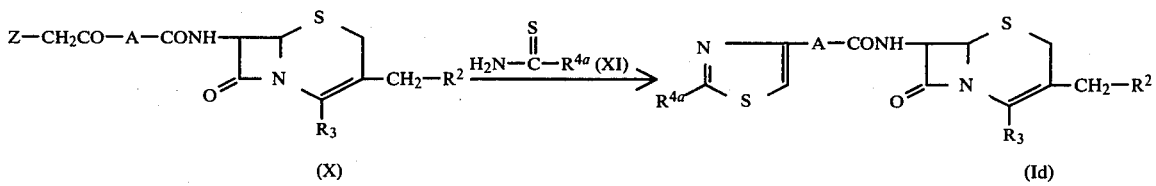

(X) → (Id)

wherein
$R^1$, $R^2$, $R^3$, $R^4$, $R^{4a}$ and A are each as defined above,
$R^{1'}$ is a heterocyclic group selected from the groups consisting of:

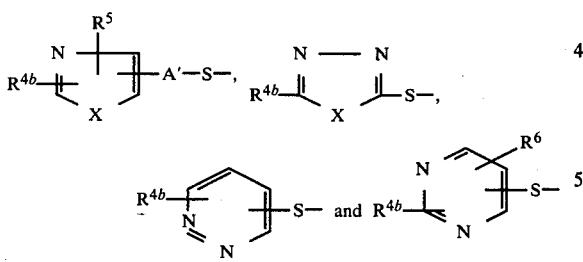

in which $R^{4b}$, $R^5$, $R^6$, A' and X are each as defined above,
$R^{2'}$ is a heterocyclic-thio group which may have suitable substituent(s),
Y is a conventional group which can be replaced by the formula: —$R^{2'}$ in which $R^{2'}$ is as defined above,
Y' is a conventional group which can be replaced by the formula: —$R^{1'}$ in which $R^{1'}$ is as defined above, and
Z is halogen.

Among the starting compounds (II) in the present invention, 3-heterocyclic-thiomethyl-7-amino-3-cephem-4-carboxylic acid compounds can be prepared by reacting 7-aminocephalosporanic acid compounds with the corresponding heterocyclic thiol compound as described in the specification of U.S. Pat. No. 3,516,997.

The other starting compounds can be prepared by the reactions which are illustrated by the following schemes.

(1)

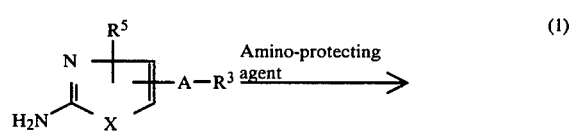

(IIIa)

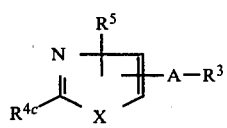

(IIIb)

(2)

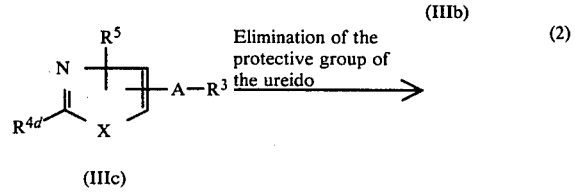

(IIIc)

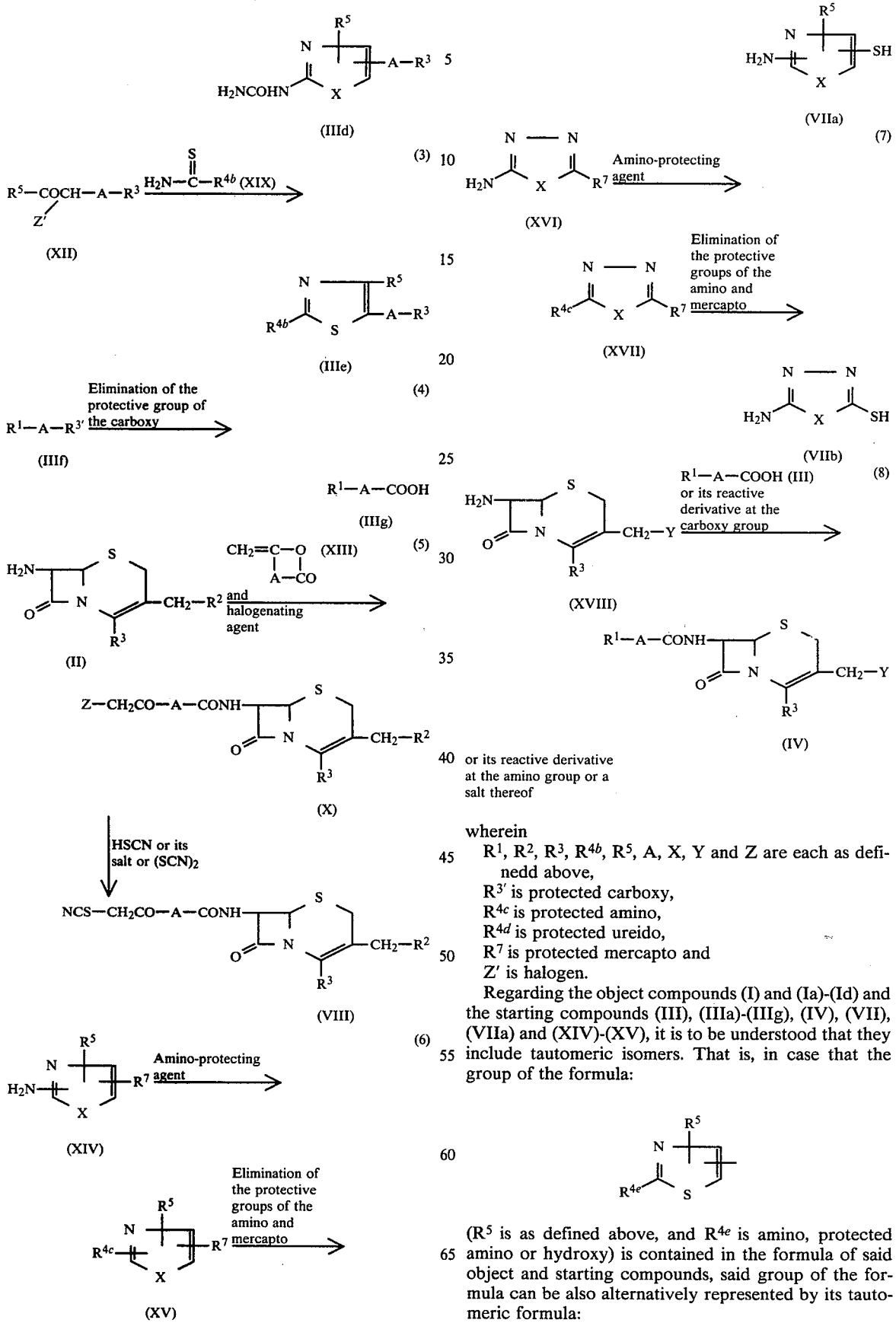

or its reactive derivative at the amino group or a salt thereof wherein
$R^1$, $R^2$, $R^3$, $R^{4b}$, $R^5$, A, X, Y and Z are each as definedd above,
$R^{3'}$ is protected carboxy,
$R^{4c}$ is protected amino,
$R^{4d}$ is protected ureido,
$R^7$ is protected mercapto and
$Z'$ is halogen.

Regarding the object compounds (I) and (Ia)-(Id) and the starting compounds (III), (IIIa)-(IIIg), (IV), (VII), (VIIa) and (XIV)-(XV), it is to be understood that they include tautomeric isomers. That is, in case that the group of the formula:

($R^5$ is as defined above, and $R^{4e}$ is amino, protected amino or hydroxy) is contained in the formula of said object and starting compounds, said group of the formula can be also alternatively represented by its tautomeric formula:

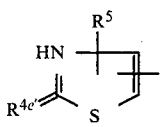

($R^5$ is as defined above, and $R^{4e'}$ is imino, protected imino or oxo), respectively. That is, both of the said groups are in the state of equilibrium and such tautomerism can be represented by the following equilibrium.

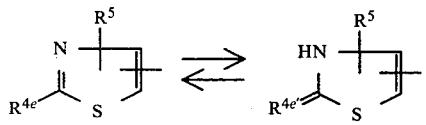

wherein $R^{4e}$, $R^{4e'}$ and $R^5$ are each as defined above.

These types of tautomerism between the amino- or hydroxy compound and the corresponding imino- or oxo-compound as stated above have been well known in the literature, and it is obvious to be skilled in the arts that both of the tautomeric isomers are easily convertible reciprocally and are included within the same category of the compound per se. Accordingly, the both of the tautomeric forms of the object compounds (I) and $(I_a)$-$(I_d)$ and the starting compounds (III), $(III_a)$-$(III_g)$, (IV), (VII), $(VII_a)$ and (XIV)-(XV) are clearly included within the scope of the present invention. In the present specification and claims, the object and starting compounds including the group of such tautomeric isomers are represented by using one of the expressions therefor, that is the formula:

" 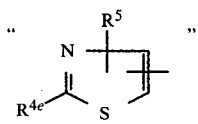 "

only for the convenient sake.

Suitable pharmaceutically acceptable salt of the object compounds (I) are conventional non-toxic salts and include a metal salt such as an alkali metal salt (e.g., sodium salt, potassium salt, etc.) and an alkaline earth metal salt (e.g., calcium salt, magnesium salt, etc.), ammonium salt, an organic base salt (e.g., trimethylamine salt, triethylamine salt, pyridine salt, picoline salt, dicyclohexylamine salt, N,N'-dibenzylethylenediamine salt, etc.), an organic acid salt (e.g., acetate, maleate, tartrate, methanesulfonate, benzenesulfonate, toluenesulfonate, etc.), an inorganic acid salt (e.g., hydrochloride, hydrobromide, sulfate, phosphate, etc.), or a salt with an amino acid (e.g., arginine, aspartic acid, glutamic acid, etc.), and the like.

In the above and subsequent descriptions of the present specification, suitable examples and illustrations of the various definitions which the present invention include within the scope thereof are explained in details as follows.

The term "lower" is intended to mean 1 to 6 carbon atoms.

Suitable lower alkyl and lower alkyl moiety in the terms "lower alkanamido(lower)alkylthiadiazolylthio", "lower alkylureido", "amino(lower)alkyl", "protected amino(lower)alkyl", "lower alkylamino" and "lower alkylimino" may include methyl, ethyl, propyl, isopropyl, butyl, pentyl, hexyl and the like.

Suitable lower alkanamido moiety in the term "lower alkanamido(lower)alkylthiadiazolylthio" may include, formamido, acetamido, propionamido, butyramido, pentanamido, isopentanamido, hexanamido and the like.

Suitable lower alkenyl moiety in the term "lower alkenyltetrazolylthio" may include vinyl, propenyl, butenyl, pentenyl, hexenyl and the like.

Suitable protected carboxy may include an ester and the like.

Suitable examples of said ester may be the ones such as lower alkyl ester (e.g., methyl ester, ethyl ester, propyl ester, isopropyl ester, butyl ester, isobutyl ester, pentyl ester, hexyl ester, 1-cyclopropylethyl ester, etc.) which may have at least one suitable substituent(s), for example, lower alkanoyloxy(lower)alkyl ester (e.g., acetoxymethyl ester, propionyloxymethyl ester, butyryloxymethyl ester, valeryloxymethyl ester, pivaloyloxymethyl ester, 2-acetoxyethyl ester, 2-propionyloxyethyl ester, etc.), lower alkanesulfonyl(lower)alkyl ester (e.g., 2-mesylethyl ester, etc.), mono(or di or tri)-halo(lower)alkyl ester (e.g., 2-iodoethyl ester, 2,2,2-trichloroethyl ester, etc.);

lower alkenyl ester (e.g., vinyl ester, allyl ester, etc.);
  lower alkynyl ester (e.g., ethynyl ester, propynyl ester, etc.);
ar(lower)alkyl ester which may have at least one suitable substituent(s) (e.g., benzyl ester, 4-methoxybenzyl ester, 4-nitrobenzyl ester, phenethyl ester, trityl ester, diphenylmethyl ester, bis(methoxyphenyl)methyl ester, 3,4-dimethoxybenzyl ester, 4-hydroxy-3,5-ditertiarybutylbenzyl ester, etc.);
aryl ester which may have at least one suitable substituent(s) (e.g., phenyl ester, tolyl ester, tertiarybutylphenyl ester, xylyl ester, mesityl ester, cumenyl ester, etc.), and the like.

Suitable lower alkylene may include methylene, ethylene, trimethylene, propylene, tetramethylene and the like.

Suitable halogen may include chlorine, bromine, iodine and fluorine.

Suitable halo(lower)alkanamido may include mono-(or di or tri)halo(lower)alkanamido (e.g., bromoacetamido, dichloroacetamido, trichloroacetamido, trifluoroacetamido, etc.), and the like.

Suitable lower alkanesulfonamido may include mesylamido, ethanesulfonamido, propanesulfonamido, isopropanesulfonamido, butanesulfonamido and the like.

Suitable arenesulfonamido may include benzenesulfonamido, toluenesulfonamido p-bromobenzenesulfonamido, m-methoxybenzenesulfonamido and the like.

Suitable protected amino and protected amino moiety in the term "protected amino(lower)alkyl" may include an amino group substituted by a conventional protecting group such as acyl as mentioned below, ar(lower)alkyl (e.g., benzyl, 4-methoxybenzyl, phenethyl, trityl, 3,4-dimethoxy benzyl, etc.) or the like.

Suitable acyl and acyl moiety in the term "acyloxy" may include carbamoyl, aliphatic acyl group and acyl group containing an aromatic or heterocyclic ring. And, suitable examples of the said acyl may be lower alkanoyl (e.g., formyl, acetyl, propionyl, butyryl, isobutyryl, valeryl, isovaleryl, oxalyl, succinyl, pivaloyl, etc.);

lower alkoxycarbonyl (e.g., methoxycarbonyl, ethoxycarbonyl, propoxycarbonyl, 1-cyclopropylethoxycarbonyl, isopropoxycarbonyl, butoxycarbonyl, tertiarybutoxycarbonyl, pentyloxycarbonyl, hexyloxycarbonyl, etc.);

lower alkanesulfonyl (e.g., mesyl, ethanesulfonyl, propanesulfonyl, isopropanesulfonyl, butanesulfonyl, etc.);

arenesulfonyl (e.g., benzenesulfonyl, tosyl, etc.);

aroyl (e.g., benzoyl, toluoyl, naphthoyl, phthaloyl, indancarbonyl, etc.);

ar(lower)alkanoyl (e.g., phenylacetyl, phenylpropionyl, etc.);

ar(lower)alkoxycarbonyl (e.g., benzyloxycarbonyl, etc.), and the like. The acyl moiety as stated above may have at least one suitable substituent(s) such as halogen (e.g., chlorine, bromine, iodine or fluorine), cyano, lower alkyl (e.g., methyl, ethyl, propyl, isopropyl, butyl, etc.), lower alkenyl (e.g., vinyl, allyl, etc.), or the like, suitable examples of which may be mono(or di or tri)halo(lower)alkanoyl (e.g., trifluoroacetyl, etc.).

Suitable heterocyclic group in the term "a heterocyclicthio group which may have suitable substituent(s)" means saturated or unsaturated, monocyclic or polycyclic heterocyclic group containing at least one heteroatom such as an oxygen, sulfur, nitrogen atom and the like.

And, preferable heterocyclic group may be N-containing heterocyclic group such as unsaturated 3 to 8-membered heteromonocyclic group containing 1 to 4 nitrogen atom(s) (e.g., pyrrolyl, pyrrolinyl, imidazolyl, pyrazolyl, pyridyl and its N-oxide, pyrimidyl, pyrazinyl, pyridazinyl, triazolyl, tetrazolyl, etc.);

saturated 3 to 8-membered heteromonocyclic group containing 1 to 4 nitrogen atom(s) (e.g., pyrrolidinyl, imidazolidinyl, piperidino, piperazinyl, etc.);

unsaturated condensed heterocyclic group containing 1 to 4 nitrogen atom(s) (e.g., indolyl, isoindolyl, indolizynyl, benzimidazolyl, quinolyl, isoquinolyl, indazolyl, benzotriazolyl, etc.);

unsaturated 3 to 8-membered heteromonocyclic group containing 1 to 2 oxygen atom(s) and 1 to 3 nitrogen atom(s) (e.g., oxazolyl, isoxazolyl, oxadiazolyl, etc.);

saturated 3 to 8-membered heteromonocyclic group containing 1 to 2 oxygen atom(s) and 1 to 3 nitrogen atom(s) (e.g., morpholinyl, etc.);

unsaturated condensed heterocyclic group containing 1 to 2 oxygen atom(s) and 1 to 3 nitrogen atom(s) (e.g., benzoxazolyl, benzoxadiazolyl, etc.);

unsaturated 3 to 8-membered heteromonocyclic group containing 1 to 2 sulfur atom(s) and 1 to 3 nitrogen atom(s) (e.g., thiazolyl, thiadiazolyl, etc.);

saturated 3 to 8-membered heteromonocyclic group containing 1 to 2 sulfur atom(s) and 1 to 3 nitrogen atom(s) (e.g., thiazolidinyl, etc.);

unsaturated condensed heterocyclic group containing 1 to 2 sulfur atom(s) and 1 to 3 nitrogen atom(s) (e.g., benzothiazolyl, benzothiadiazolyl, etc.) and the like, wherein said heterocyclic group may have at least one suitable substituent(s) such as lower alkyl (e.g., methyl, ethyl, propyl, isopropyl, butyl, isobutyl, pentyl, cyclopentyl, hexyl, cyclohexyl, etc.); amino(lower)alkyl (e.g., aminomethyl, aminoethyl, aminopropyl, aminobutyl, etc.); lower alkenyl (e.g., vinyl, allyl, butenyl, etc.); aryl (e.g., phenyl, tolyl, etc.); halogen (e.g., chlorine, bromine, iodine or fluorine); amino;

acylamino(lower)alkyl such as lower alkanamido(lower)alkyl (e.g., acetamidomethyl, propionamidomethyl, acetamidoethyl, etc.); and the like.

Suitable "a conventional group which can be replaced by the formula: —$R^1$" and "a conventional group which can be replaced by the formula: —$R^2$" may include an acid residue such as a halogen atom (e.g., chlorine, bromine, etc.), azido group, an acyloxy group such as lower alkanoyloxy (e.g., formyloxy, acetoxy, propionyloxy, butyryloxy, etc.) or aroyloxy (e.g., benzyloxy, toluoyloxy, etc.) or the like, and the like.

Suitable protected ureido may include an ureido group substituted by a conventional protecting group such as the protecting group as aforementioned in the explanation of protected amino;

halo(lower)alkyl such as trihalomethyl (e.g., trichloromethyl, trifluoromethyl, etc.);

lower alkylsilyl such as tri(lower)alkylsilyl (e.g., trimethylsilyl, etc.); and the like.

Suitable protected mercapto may include an mercapto group substituted by a conventional protecting group as aforementioned in the explanation of protected amino.

The various processes for preparing the object compounds of the present invention are explained in details in the following.

PROCESS 1

The object compound (I) can be prepared by reacting the compound (II) or its reactive derivative at the amino group or a salt thereof with the compound (III) or its reactive derivative at the carboxy group, and then optionally subjecting the resulting compound to elimination reaction of the protective group of the amino.

Suitable reactive derivative at the amino group of the compound (II) may include Schiff's base type imino or its tautomeric enamine type isomer formed by the reaction of the compound (II) with a carbonyl compound; a silyl derivative formed by the reaction of the compound (II) with a silyl compound such as bis(trimethylsilyl)acetamide or the like; a derivative formed by reaction of the compound (II) with phosphorus trichloride or phosgene, and the like.

Suitable salt of the compound (II) may include an acid addition salt such as an organic acid salt (e.g., acetate, maleate, tartrate, benzenesulfonate, toluenesulfonate, etc.) or an inorganic acid salt (e.g., hydrochloride, hydrobromide, sulfate, phosphate, etc.); a metal salt (e.g., sodium salt, potassium salt, calcium salt, magnesium salt, etc.); ammonium salt; an organic amine salt (e.g., triethylamine salt, dicyclohexylamine salt, etc.), and the like.

Suitable reactive derivative at the carboxy group of the compound (III) may include an acid halide, an acid anhydride, an activated amide, an activated ester, and the like. The suitable example may be an acid chloride, an acid azide; a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkylcarbonic acid, aliphatic carboxylic acid (e.g., pivalic acid, pentanoic acid, isopentanoic acid, 2-ethylbutyric acid or trichloroacetic acid, etc.) or aromatic carboxylic acid (e.g., benzoic acid, etc.); a symmetrical acid anhydride; an activated amide with imidazole, 4-substituted imidazole, dimethylpyrazole, triazole or tetrazole; or an activated ester (e.g., cyanomethyl ester, methoxymethyl ester, dimethyliminomethyl [$(CH_3)_2N^+=CH-$] ester, vinyl ester, propargyl ester, p-nitrophenyl ester, 2,4-dinitrophenyl ester, trichlorophenyl ester, pentachlorophenyl ester, mesyl phenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.), or an ester with N,N-dimethylhydroxylamine, 1-hydroxy-2-(1H)-pyridone, N-hydroxysuccinimide, N-hydroxyphthalimide or 1-hydroxy-6-chloro-1H-benzotriazole, and the like. These reactive derivatives can be optionally selected from them according to the kind of the compound (III) to be used.

The reaction is usually carried out in a conventional solvent such as water, acetone, dioxane, acetonitrile, chloroform, methylene chloride, ethylene chloride, tetrahydrofuran, ethyl acetate, N,N-dimethyl formamide, pyridine or any other organic solvent which does not adversely influence to the reaction. Among these solvents, hydrophilic solvents may be used in a mixture with water.

When the compound (III) is used in free acid form or its salt form in the reaction, the reaction is preferably carried out in the presence of a conventional condensing agent such as N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, N,N-carbonylbis(2-methylimidazole), pentamethyleneketene-N-cyclohexylimine, diphenylketene-N-cyclohexylimine, alkoxyacetylene, 1-alkoxy-1-chloroethylene, trialkyl phosphite, ethyl polyphosphate, isopropyl polyphosphate, phosphorus oxychloride, phosphorus trichloride, thionyl chloride, oxalyl chloride, triphenylphosphine, 2-ethyl-7-hydroxybenzisoxazolium salt, 2-ethyl-5-(m-sulfophenyl)isoxazolium hydroxide intramolecular salt, (chloromethylene)dimethylammonium chloride, 1-(p-chlorobenzenesulfonyloxy)-6-chloro-1H-benzotriazole, or the like.

The reaction may be also carried out in the presence of an inorganic or organic base such as an alkali metal bicarbonate, tri(lower)alkylamine, pyridine, N-(lower)alkylmorphorine, N,N-di(lower)alkylbenzylamine, or the like. The reaction temperature is not critical, and the reaction is usually carried out under cooling or at room temperature.

When the resulting compound has a protected amino group, it may be optionally subjected to elimination reaction of the protective group of the amino.

The optional elimination reaction is carried out in accordance with a conventional method such as hydrolysis, reduction, or the like. The hydrolysis may also include a method using an acid or base or hydrazine and the like. These methods may be selected depending on the kind of the protective groups to be eliminated.

Among these methods, hydrolysis using an acid is one of the most common and preferable method for eliminating the protective groups such as substituted or unsubstituted alkoxycarbonyl, cycloalkoxycarbonyl, substituted or unsubstituted aralkoxycarbonyl, aralkyl (e.g., trityl), substituted phenylthio, substituted aralkylidene, substituted alkylidene, substituted cycloalkylidene or the like. Suitable acid include an organic or inorganic acid such as formic acid, trifluoroacetic acid, benzenesulfonic acid, p-toluenesulfonic acid, hydrochloric acid and the like, and the most suitable acid is an acid which can be easily removed from the reaction mixture by a conventional manner such as distillation under reduced pressure, for example, formic acid, trifluoroacetic acid, etc. The acids can be selected according to the kind of the protected group to be eliminated. When the elimination reaction is conducted with an acid, it can be carried out in the presence or absence of a solvent. Suitable solvent include water, a conventional organic solvent or a mixture thereof. The hydrolysis using hydrazine is commonly applied for eliminating a phthaloyl type amino-protective group.

The reductive elimination is generally applied for eliminating the protective group, for example, haloalkoxycarbonyl (e.g., trichloroethoxycarbonyl, etc.), substituted or unsubstituted aralkoxy carbonyl (e.g., benzyloxycarbonyl, etc.), 2-pyridylmethoxycarbonyl, etc. Suitable reduction may include, for example, reduction with an alkali metal borohydride (e.g., sodium borohydride, etc.), reduction with a combination of a metal (e.g., tin, zinc, iron, etc.) or the said metal together with a metal salt compound (e.g., chromous chloride, chromous acetate, etc.) and an organic or inorganic acid (e.g., acetic acid, propionic acid, hydrochloric acid, etc.); and catalytic reduction. Suitable catalyst include a conventional one, for example, Raney nickel, platinum oxide, palladium on charcoal and the like.

Among the protective groups, the acyl group can be generally eliminated by hydrolysis. Especially, trifluoroacetyl group can be easily eliminated by treating with water even in around neutral condition, and halogen substituted-alkoxycarbonyl and 8-quinolyloxycarbonyl groups are usually eliminated by treating with a heavy metal such as copper, zinc, or the like.

The reaction temperature is not critical and may be suitably selected in accordance with the kind of the protective group for the amino group and the elimination method as mentioned above, and the reaction is preferably carried out under a mild condition such as under cooling or slightly elevated temperature.

The present invention includes, within its scope, the cases that the protected carboxy is transformed into the free carboxy group during the reaction or the post-treating step of the present process.

PROCESS 2

The object compound ($I_a$) can be prepared by reacting the compound (IV) with the compound (V) or its reactive derivative at the mercapto group.

The starting compound (IV) used in the present process can be prepared by reacting the compound (XVIII) or its reactive derivative at the amino group or a salt thereof with the compound (III) or its reactive derivative at the carboxy group. The reaction conditions for preparing the starting compound (IV) are the substantially same as those for preparing the compound (I) as stated in the explanation of Process 1, and therefore the details therefor are to be referred to the explanation of Process 1 by reading "the compound (II)" as "the compound (IX)" for the convenient sake. That is, suitable reactive derivative at the amino group and salt of the compound (XVIII) is the same as that of the compound (II), and the reaction conditions are also the same as those used in Process 1.

Suitable reactive derivative at the mercapto group of the compound (V) may include a metal salt such as an alkali metal salt (e.g., sodium salt, potassium salt, etc.), an alkaline earth metal salt (e.g., magnesium salt, etc.) or the like.

The reaction of the compound (IV) with the compound (V) or its reactive derivative at the mercapto group may be preferably carried out in a conventional solvent such as water, acetone, chloroform, nitrobenzene, dimethylformamide, methanol, ethanol, dimethylsulfoxide, or any other rather high polar solvents which do not adversely influence to the reaction, and a mixture thereof. The reaction is preferably carried out in around neutral condition. When the compound (IV) and/or the compound (V) are used in a free form, the reaction is preferably conducted in the presence of an organic or inorganic base such as alkali metal hydroxide, alkali metal carbonate, alkali metal bicarbonate, trialkylamine, pyridine or the like. The reaction temperature is not critical, and the reaction is usually carred out at room temperature or slightly elevated temperature.

The present invention may include, within its scope, the cases that the protected amino group and/or the protected carboxy group are transformed into the corresponding free amino group and/or carboxy group during the reaction or the post-treating step in the present process.

PROCESS 3

The object compound ($I_b$) can be prepared by reacting the compound (VI) with the compound (VII) or its reactive derivative at the mercapto group.

Suitable reactive derivative at the mercapto group of the compound (VII) is the same as that of the compound (V) in the Process 2.

The present reaction can be carried out in substantially the same conditions as those used in the reaction of the Process 2, and therefore the details therefor are to be referred to the explanation for the Process 2, respectively.

PROCESS 4

The object compound ($I_c$) can be prepared by reacting the compound (VIII) with the compound (IX).

The starting compound (VIII) used in the present process can be prepared by reacting the compound (X) with thiocyanic acid or its salt or thiocyanogen, as shown in the reaction scheme (5).

The reaction can be usually carried out in a conventional solvent such as water, acetone, chloroform, methylene chloride, tetrahydrofuran, ethyl acetate, N,N-dimethyl formamide, dimethyl sulfoxide, lower alkanol or any other solvent which does not adversely influence to the reaction. The reaction is preferably carried out in a presence of a dehydrohalogenation agent such as silver fluoroborate, silver isocyanate, silver perchlorate, silver acetate, a base (e.g., trialkylamine, pyridine, etc.). The reaction temperature is not critical, and the reaction is usually carried out at room temperature or slightly elevated temperature.

The reaction of the compound (VIII) with the compound (IX) can be carried out in a conventional solvent such as acetone, acetonitrile, chloroform, methylene chloride, tetrahydrofuran, ethyl acetate, N,N-dimethyl formamide, dimethyl sulfoxide, lower alkanol or any other solvent which does not adversely influence to the reaction.

The reaction is preferably carried out in the presence of an organic or inorganic acid (e.g., acetic acid, propionic acid, hydrochloric acid, phosphoric acid, sulfuric acid, etc.); or an organic or inorganic base (e.g., alkali metal hydroxide, alkali metal carbonate, alkali metal bicarbonate, trialkylamine, pyridine, etc.) or an acidic or basic buffer solution thereof; The reaction temperature is not critical, and the reaction is usually carried out at room temperature or slightly elevated temperature.

PROCESS 5

The object compound ($I_d$) can be prepared by reacting the compound (X) with the compound (XI) or its reactive derivative.

The starting compound (X) used in the present process can be prepared by reacting the compound (II) with the compound (XIII) and a halogenating agent, as shown in the reaction scheme (5).

Suitable halogenating agent include halogen (e.g., bromine, chlorine, iodine, etc.), N-haloamide (e.g., N-bromoacetamide, etc.), N-haloimide (e.g., N-bromosuccinimide, N-chlorosuccinimide, etc.) or the like. The reaction may be preferably carried out in a conventional solvent such as methylene chloride, chloroform, acetic acid, N,N-dimethylformamide, N,N-dimethyl sulfoxide, or any other solvent which does not adversely influence to the reaction. The reaction temperature is not critical, and the reaction is usually carried out under a mild condition such as under cooling or slightly elevated temperature.

Suitable reactive derivative of the compound (XI) may include a metal salt such as an alkali metal salt (e.g., sodium salt, potassium salt, etc.), an alkaline earth metal salt (e.g., magnesium, etc.) or the like.

The reaction of the compound (X) with the compound (XI) may be preferably carried out in a conventional solvent such as water, acetone, chloroform, nitrobenzene, N,N-dimethylformamide, methanol, ethanol, dimethyl sulfoxide, or any other rather high polar solvent which does not adversely influence to the reaction, and the mixture thereof. The reaction is preferably carried out in around neutral condition. When the compound (X) and/or the compound (XI) are used in a free form, the reaction is preferably conducted in the presence of an organic or inorganic base such as alkali metal hydroxide, alkali metal carbonate, alkali metal bicarbonate, trialkylamine, pyridine or the like. The reaction temperature is not critical, and the reaction is usually carried out at room temperature or slightly elevated temperature.

Processes for preparing the starting compounds ($III_b$), ($III_d$), ($III_e$), ($III_g$), ($VII_a$), ($VII_b$), (XV) and (XVIII) are explained in details as follows.

The starting compounds ($III_b$) can be prepared by reacting the compound ($III_a$) or its reactive derivative at the amino group or a salt thereof with an amino-protecting agent, the starting compound (XV) can be prepared by reacting the compound (XIV) or its reactive derivative at the amino group or a salt thereof with an amino-protecting agent and the starting compound (XVII) can be prepared by reacting the compound (XVI) or its reactive derivatives at the amino group or a salt thereof with an amino-protecting agent, respectively. Suitable reactive derivative at the amino group of the compounds ($III_a$), (XIV) and (XVI) and suitable salt of the compounds ($III_a$), (XIV) and (XVI) may include the same ones as illustrated in the explanations of reactive derivative at the amino group of the compound (II) or (XVIII) and salt of the compound (II) or (XVIII), respectively.

Suitable amino-protecting agent may include acylating agent which may include an aliphatic, aromatic and heterocyclic carboxylic acid, and the corresponding sulfonic acid, carbonic acid ester and carbamic acid, and the corresponding thio acid thereto, and the reactive derivative of the above acids, and an aliphatic, aromatic and heterocyclic isocyanate; and an activated reactive derivative of ar(lower)alkanol such as ar(lower)alkyl halide (e.g., benzyl chloride, diphenylmethyl bromide, trityl chloride, 4-methoxybenzyl bromide, etc.); and the like.

Suitable reactive derivative of the above acids may include the same ones as illustrated in the explanation of "reactive derivative at the carboxy group of the compound (III)". The example of the amino-protecting group introduced into the amino group in the compounds ($III_a$), (XIV) and (XVI) by the afore-mentioned amino-protecting agent may be the same ones as illustrated in the explanation of the protective group in the term "protected amino".

The present reaction can be carried out in the similar manner as illustrated in the reaction of the Process 1.

The starting compound ($III_d$) can be prepared by subjecting the compound ($III_c$) to elimination reaction of the protective group of the ureido.

The elimination reaction is carried out in accordance with a conventional method such as hydrolysis or the like. The hydrolysis is preferably carried out in a presence of a base or an acid. Suitable base may include an inorganic base and an organic base such as an alkali metal (e.g., sodium, potassium, etc.), an alkaline earth metal (e.g., magnesium, calcium, etc.), the hydroxide or carbonate or bicarbonate thereof, trialkylamine (e.g., trimethylamine, triethylamine, etc.), picoline, 1,5-diazabicyclo[4,3,0]none-5-ene, 1,4-diazabicyclo[2,2,2]octane, 1,8-diazabicyclo[5,4,0]undecene-7, or the like. Suitable acid may include an organic acid (e.g., formic acid, acetic acid, propionic acid, etc.) and an inorganic acid (e.g., hydrochloric acid, hydrobromic acid, sulfuric acid, etc.).

The reaction temperature is not critical, and the reaction is usually carried out at room temperature or slightly elevated temperature.

The starting compound ($III_e$) can be prepared by reacting the compound (XII) with the compound (XIX) or its reactive derivative.

Suitable reactive derivative of the compound (XIX) is the same as that of the compound (XI) in the Process 5, and the present reaction can be carried out in the similar manners to those used in the reaction of the Process 5, and therefore the details therefor can be also referred to the explanation for the Process 5.

The starting compound ($III_g$) can be prepared by subjecting the compound ($III_f$) to elimination reaction of the protective group of the carboxy.

In the present elimination reaction, all conventional methods used in the elimination reaction of the protected carboxy, for example, hydrolysis, reduction, etc. can be applicable.

Hydrolysis is preferably carried out in the presence of a base or an acid. Suitable base may include an inorganic base and an organic base such as an alkali metal (e.g., sodium, potassium, etc.), an alkaline earth metal (e.g., magnesium calcium, etc.), the hydroxide or carbonate or bicarbonate thereof, trialkylamine (e.g., trimethylamine, triethylamine, etc.), picoline, 1,5-diazabicyclo[4,3,0]none-5-ene, 1,4-diazabicyclo[2,2,2]-octane, 1,8-diazabicyclo[5,4,0]undecene-7, or the like. Suitable acid may include an organic acid (e.g., formic acid, acetic acid, propionic acid, etc.) and an inorganic acid (e.g., hydrochloric acid, hydrobromic acid, sulfuric acid, etc.). The reduction can be applied for elimination of the protective group such as halo(lower)alkyl ester (e.g., 2-iodoethyl ester, 2,2,2-trichloroethyl ester, etc.), or the like. The reduction method include, reduction using a combination of a metal (e.g., zinc, zinc amalgam, etc.) or a chrome salt compound (e.g., chromous chloride, chromous acetate, etc.) and an organic or inorganic acid (e.g., acetic acid, propionic acid, hydrochloric acid, etc.), and a conventional catalytic reduction. The catalysts for catalytic reduction include, for example, platinum catalyst (e.g., platinum wire, spongy platinum, platinum black, platinum colloid, etc.), palladium catalyst (e.g., spongy palladium, palladium black, palladium oxide, palladium on barium sulfate, palladium on barium carbonate, palladium on charcoal, palladium on silica gel, palladium colloid, etc.), nickel catalyst (e.g., reduced nickel, nickel oxide, Raney nickel, Urushibara nickel, etc.), and the like.

The reaction temperature is not critical, and it may be suitably selected in accordance with the kind of the protective group of the carboxy and the elimination method.

The starting compound ($VII_a$) can be prepared by subjecting the compound (XV) to elimination reaction of the protective groups of the amino and mercapto and the starting compound ($VII_b$) can be prepared by subjecting the compound (XVII) to elimination reaction of the protective groups of the amino and mercapto, respectively.

The elimination reaction is carried out in accordance with a conventional method such as hydrolysis including a method using an acid or base or hydrazine and the like, reduction, or the like. These methods may be selected depending on the kind of the protective groups to be eliminated.

Among these methods, hydrolysis using an acid is one of the most common and preferable method for eliminating the protective groups such as substituted or unsubstituted alkoxycarbonyl, cycloalkoxycarbonyl, substituted or unsubstituted aralkoxycarbonyl, aralkyl (e.g., trityl, etc.), substituted phenylthio, substituted aralkylidene, substituted alkylidene, substituted cycloalkylidene or the like. Suitable acid may include an organic or inorganic acid such as formic acid, trifluoroacetic acid, benzenesulfonic acid, p-toluenesulfonic acid, hydrochloric acid and the like, and the most suitable acid is an acid which can be easily removed from the reaction mixture by a conventional manner such as distillation under reduced pressure, for example, formic acid, trifluoroacetic acid, etc. The acids can be selected according to the kind of protected group to be eliminated. When the elimination reaction is conducted with an acid, it can be carried out in the presence or absence of a solvent. Suitable solvent may include water, a conventional organic solvent or a mixed solvent thereof. The hydrolysis using hydrazine is commonly applied for eliminating a phthaloyl type amino-protective group.

The reductive elimination is generally applied for eliminating the protective group, for example, haloalkoxycarbonyl (e.g., trichloroethoxycarbonyl, etc.), substituted or unsubstituted aralkoxycarbonyl (e.g., benzyloxycarbonyl, etc.), 2-pyridylmethoxycarbonyl, etc. Suitable reduction may include, for example, reduction with an alkali metal borohydride (e.g., sodium borohydride, etc.), reduction with a combination of a metal (e.g., tin, zinc, iron, etc.) or the said metal together with a metal salt compound (e.g., chromous chloride, chromous acetate, etc.) and an organic or inorganic acid (e.g., acetic acid, propionic acid, hydrochloric acid, etc.); and catalytic reduction. Suitable catalyst include a conventional one, for example, Raney nickel, platinum oxide, palladium on charcoal and the like.

Among the protective groups, the acyl group can be generally eliminated by hydrolysis. Especially, trifluoroacetyl group can be easily eliminated by treating with water even in around neutral condition, and halogen substituted-alkoxycarbonyl and 8-quinolyloxycarbonyl groups are usually eliminated by treating with a heavy metal such as copper, zinc, or the like.

The reaction temperature is not critical and may be suitably selected in accordance with the kind of the protective groups for the amino and mercapto groups and the elimination method as mentioned above, and the reaction is preferably carried out under a mild condition such as under cooling or slightly elevated temperature.

In the aforementioned reactions and/or the posttreating steps of the processes of the present invention, the aforementioned tautoneric isomers may occasionally transformed into the other tautomeric isomers, and such cases are also included in the scope of the present invention.

In case that the object compound (I) is obtained in a form of the free acid at 4 position and/or in case that the object compound (I) has free amino group, it may be transformed into its pharmaceutically acceptable salt as aforementioned by a conventional method.

The object compounds (I) of the present invention exhibit high antibacterial activity and inhibit the growth of a number of microorganisms including Gram-positive and Gram-negative bacteria. For therapeutic purpose, the cephalosporin compounds according to the present invention can be used in the form of pharmaceutical preparation which contain said compounds in admixture with a pharmaceutically acceptable carriers such as an organic or inorganic solid or liquid excipient suitable for oral, parenteral or external administration. The pharmaceutical preparations may be capsules, tables, dragees, ointments or suppositories, solutions, suspensions, emulsions, and the like. If desired, there may be included in the above preparations auxiliary substances, stabilizing agents, wetting or emulsifying agents, buffers and other commonly used additives.

While the dosage of the compounds will vary from and also depend upon the age and condition of the patient, an average single dose of about 10 mg., 50 mg., 100 mg., 250 mg., 500 mg., and 1000 mg. of the compounds according to the present invention has proved to be effective for treating infectious diseases caused by pathogenic bacteria.

In order to illustrate the usefulness of the object compounds, anti-microbial activities of some representative compounds of the present invention against some test strains of pathogenic bacteria are shown in their minimal inhibitory concentrations below.

TEST METHOD

In vitro antibacterial activity was determined by the two-fold agar-plate dilution method as described below.

One loopful of an overnight culture of each test strain in Trypticase-soy broth ($10^8$ viable cells per ml.) was streaked on heart infusion agar (HI-agar) containing graded concentrations of representative antibiotic, and the minimal inhibitory concentration (MIC) was expressed in terms of $\mu g$/ml. after incubation at 37° C. for 20 hours.

TEST COMPOUNDS AND RESULTS (1) 3-(1-Methyl-1H-tetrazol-5-yl)thomethyl-7-(2-methanesulfonamidothiazol-4-yl)acetamido-3-cephem-4-carboxylic acid Kl. aerogenes 428: 0.39

(2) 3-Carbamoyloxymethyl-7-(2-aminothiazol-4-yl)acetamido-3-cephem-4-carboxylic acid Pr.vulgaris 84: 6.25

(3) 3-(1-Methyl-1H-tetrazol-5-yl)thiomethyl-7-(5-amino-2H-tetrazol-2-yl)acetamido-3-cephem-4-carboxylic acid B. subtilis ATCC-6633: 0.2

(4) 3-(5-Methyl-1,3,4-thiadiazol-2-yl)thiomethyl-7-(5-aminomethyl-1,3,4-thiadiazol-2-yl)thioacetamido-3-cephem-4-carboxylic acid B. subtilis ATCC-6633: 0.2

The following examples are given for the purpose of illustrating the present invention:

EXAMPLE 1

A suspension of 2-aminothiazol-4-ylacetic acid (1.8 g.) in dried methylene chloride (32 ml.) was stirred under ice-cooling, and to the suspension was introduced dried hydrogen chloride gas for 20 minutes. To the mixture was gradually added phosphorus pentachloride (5.93 g.) under ice-cooling and the mixture was stirred for 20 minutes at room temperature and then the solvent was distilled off at room temperature. The resulting oily substance was dissolved in dried acetone (10 ml.), and the solution was dropwise added to a solution of 3-(benzimidazol-2-yl)thiomethyl-7-amino-3-cephem-4-carboxylic acid (3.62 g.) and triethylamine (3.02 g.) in a mixture of acetone and water (1:1), (36 ml.) over 20 minutes under ice-cooling and stirring while the mixture was kept to pH 7.5 to 8.0 with triethylamine. The mixture was further stirred for 30 minutes at the same temperature, then adjusted to pH 3.5 with 10% hydrochloric acid. The precipitates were collected by filtration and added to a mixture of acetone (100 ml.) and water (100 ml.) and then the mixture was stirred for 30 minutes. After filtration of the mixture, the filtrate was concentrated until the volume of the filtrate became about 50 ml. The precipitates were collected by filtration, washed with water and then dried to give pale yellow powder of 3-(benzimidazol-2-yl)thiomethyl-7-(2-aminothiazol-4-yl)acetamido-3-cephem-4-carboxylic acid (0.7 g.).

IR Spectrum (Nujol): 3100–3500, 1775, 1665 cm$^{-1}$.

NMR Spectrum (D$_2$O-N$_a$HCO$_3$, δ): 6.9–7.7, (4H, m), 6.54, (1H, s), 5.67, (1H, d, J=5 Hz), 5.04, (1H, d, J=5 Hz), 4.22, (2H, ABq, J=13 Hz), 3.1–4.1, (4H, m).

EXAMPLE 2

To a suspension of 2-aminothiazol-4-ylacetic acid (1.2 g.) in dried methylene chloride (75 ml.) was introduced dried hydrogen chloride gas under ice-cooling and stirring to produce 2-aminothiazol-4-ylacetic acid hydrochloride, and to the mixture was gradually added phosphorus pentachloride (4.0 g.) under ice-cooling and stirring and the mixture was stirred for 1 to 2 hours at room temperature. After removal of methylene chloride from the mixture, to the residue was added dried benzene and then the solvent was distilled off. The residue was dissolved in dried acetone (20 ml.), and the solution was dropwise added to a solution of 3-(1-allyl-1H-tetrazol-5-yl)thiomethyl-7-amino-3-cephem-4-carboxylic acid (1.8 g.) and sodium bicarbonate (2.1 g.) in a mixture of acetone (25 ml.) and water (25 ml.) under ice-cooling and stirring while the mixture was kept to pH 7.5 to 8.5 with triethylamine. The mixture was further stirred for 20 minutes, and acetone was removed at low temperature.

The remaining mixture was washed with ethyl acetate and the aqueous mixture was adjusted to pH 2 with 10% hydrochloric acid. The precipitates were collected by filtration and dried to give pale yellow powder of 3-(1-allyl-1H-tetrazol-5-yl)thiomethyl-7-(2-aminothiazol-4-yl)acetamido-3-cephem-4-carboxylic acid (0.7 g.).

IR Spectrum (Nujol): 3200–3500, 1775, 1670 $cm^{-1}$.

NMR Spectrum ($D_2O$-$N_aHCO_3$, δ): 6.55, (1H, s), 5.5–6.1, (1H, m), 5.62 (1H, d, J=4 Hz), 4.3–5.3, (4H, m), 5.10 (1H, d, J=4 Hz), 3.9–4.55, (2H, m), 3.2–4.1 (4H, m).

EXAMPLE 3

To a suspension of 2-amino-4-methylthiazol-5-ylacetic acid (2.2 g.) in dried methylene chloride (80 ml.) was introduced dried hydrogen chloride gas for 10 minutes under ice-cooling, and to the mixture was gradually added phosphorus pentachloride (6.1 g.). The mixture was stirred at room temperature until it became a solution, and then methylene chloride was distilled off. After addition of dried benzene to the residue, the mixture was concentrated under reduced pressure. The residue was triturated in a mixture of dried acetone and n-hexane, and thus obtained powder was collected by filtration, washed with n-hexane and then dried. The powder was gradually added to a solution of 3-(1-methyl-1H-tetrazol-5-yl)-thiomethyl-7-amino-3-cephem-4-carboxylic acid (3.3 g.) and sodium bicarbonate (4.2 g.) in a mixture of acetone (40 ml.) and water (40 ml.) under ice-cooling and stirring while the mixture was kept to pH 7 to 8.2 with 20% sodium carbonate aqueous solution. The mixture was further stirred for 30 minutes and washed with benzene. After addition of ethyl acetate to the resulting mixture, the mixture was adjusted to pH 6 with 10% hydrochloric acid and then washed with ethyl acetate. After further addition of ethyl acetate to the resulting mixture, the mixture was adjusted to pH 2 with 10% hydrochloric acid, and then the precipitated insoluble substance was filtered off and washed with water. The aqueous layer was separated from the filtrate and combined with aqueous washings. The aqueous layer was concentrated at low temperature under reduced pressure, and the precipitates were collected by filtration and then dried to give yellowish brown powder of 3-(1-methyl-1H-tetrazol-5-yl)thiomethyl-7-(2-amino-4-methylthiazol-5-yl)acetamido-3-cephem-4-carboxylic acid (1.8 g.).

IR Spectrum (Nujol): 3200–3500, 1770, 1670 $cm^{-1}$.

NMR Spectrum ($D_2O$-$N_aHCO_3$, δ): 5.70, (1H, d, J=5 Hz), 5.17, (1H, d, J=5 Hz), 4.27, (2H, ABq, J=14 Hz), 4.10, (3H, s), 3.75, (2H, s), 3.66 (2H, ABq, J=18 Hz), 2.18, (1H, s).

EXAMPLE 4

To a suspension of 2-trifluoroacetamidothiazol-4-ylacetic acid (2.54 g.) in dried methylene chloride (90 ml.) was gradually added phosphorus pentachloride (4.12 g.) under ice-cooling and stirring, and the mixture was further stirred for 5 hours. The precipitated solid was collected by filtration, washed with n-hexane and then dried. Thus obtained solid was gradually added to a solution of 3-(5-methyl-1,3,4-thiadiazol-2-yl)thiomethyl-7-amino-3-cephem-4-carboxylic acid (3.1 g.) and sodium bicarbonate (3.8 g.) in a mixture of acetone (40 ml.) and water (40 ml.) under ice-cooling and stirring while the mixture was kept to pH 7 to 8 with 20% sodium carbonate aqueous solution. The mixture was further stirred for 30 minutes and washed with benzene. After addition of ethyl acetate to the resulting mixture, the mixture was adjusted to pH 6 with 10% hydrochloric acid, and then washed with ethyl acetate. After further addition of ethyl acetate to the mixture, the mixture was adjusted to pH 2 with 10% hydrochloric acid, and then the insoluble substance was filtered off. The ethyl acetate layer was separated from the filtrate, washed with an aqueous solution of sodium chloride and then dried over magnesium sulfate. After distillation of ethyl acetate from the ethyl acetate layer, to the residue was added ethyl ether, and the precipitates were collected by filtration and then dried to give white powder of 3-(5-methyl-1,3,4-thiadiazol-2-yl)thiomethyl-7-(2-trifluoroacetamido-thiazol-4-yl)acetamido-3-cephem-4-carboxylic acid (1.8 g.).

IR Spectrum (Nujol): 3150–3300, 1780, 1720, 1670 $cm^{-1}$.

NMR Spectrum ($D_2O$-$N_aHCO_3$, δ): 7.00, (1H, s), 5.66, (1H, d, J=5 Hz), 5.08, (1H, d, J=5 Hz), 4.21, (2H, ABq, J=14 Hz), 3.81, (2H, s), 3.53, (2H, ABq, J=17 Hz), 2.73, (3H, s).

EXAMPLE 5

To a suspension of 2-amino-4-methylthiazol-5-ylacetic acid hydrobromide (1.5 g.) in dried methylene chloride (30 ml.) was gradually added phosphorus pentachloride (3.25 g.) under ice-cooling and stirring, and the mixture was stirred until it became a solution, and then methylene chloride was distilled off. After addition of dried benzene to the residue, the mixture was evaporated. The residue was dissolved in dried acetone (20 ml.), which still includes insoluble substance, and thus obtained solution was dropwise added to a solution of 3-(5-methyl-1,3,4-thiadiazol-2-yl)thiomethyl-7-amino-3-cephem-4-carboxylic acid (1.72 g.) and sodium bicarbonate (2.1 g.) in a mixture of acetone (20 ml.) and water (20 ml.) under ice-cooling and stirring while the mixture was kept to pH 7 to 8.5 with 20% sodium carbonate aqueous solution. The mixture was further stirred for 30 minutes and washed with benzene, and then the mixture was treated with the similar manner as described in Example 3 to give yellowish brown powder of 3-(5-methyl-1,3,4-thiadiazol-2-yl)thiomethyl-7-(2-amino-4-methylthiazol-5-yl)acetamido-3-cephem-4-carboxylic acid (0.3 g.).

IR Spectrum (Nujol): 3200–3500, 1770, 1645 $cm^{-1}$.

NMR Spectrum ($D_2O$-$N_aHCO_3$, δ): 5.60, (1H, d, J=5 Hz), 5.06, (1H, d, J=5 Hz), 4.21, (2H, ABq, J=14 Hz), 3.65, (2H, s), 3.56, (2H, ABq, J=17 Hz), 2.72, (3H, s), 2.13, (3H, s).

EXAMPLE 6

To a suspension of 2-aminothiazol-5-ylacetic acid (2.36 g.) in dried methylene chloride (20 ml.) was introduced dried hydrogen chloride gas over about 5 minutes under ice-cooling and stirring, and to the mixture was gradually added phosphorus pentachloride (3.74 g.) under ice-cooling and stirring. The mixture was stirred at room temperature until the mixture became a homogeneous solution, and then methylene chloride was distilled off under reduced pressure. After addition of benzene (10 ml.) to the residue, the solvent was removed. The oily residue was dissolved in dried acetone (40 ml.), and the solution was dropwise added to a solution of 3-(1-methyl-1H-tetrazol-5-yl)thiomethyl-7-amino-3-cephem-4-carboxylic acid (3.28 g.) and sodium bicarbonate (4.2 g.) in a mixture of acetone (40 ml.) and water (40 ml.) under ice-cooling and stirring while the mixture was kept to pH 7.5 to 8.0 with 20% sodium carbonate aqueous solution. The mixture was further stirred for about 30 minutes at the same temperature. After the reaction, the reaction mixture was filtered and the filtrate was adjusted to pH 3 with diluted hydrochloric acid under ice-cooling and stirring. The precipitates were collected by filtration and dissolved in a mixture of acetone (25 ml.) and water (25 ml.). The solution was treated with activated carbon and filtered. The filtrate was concentrated under reduced pressure, and the precipitates were collected by filtration and then dried to give light brown powder of 3-(1-methyl-1H-tetrazol-5-yl)thiomethyl-7-(2-aminothiazol-5-yl)-acetamido-3-cephem-4-carboxylic acid (1.2 g.).

IR Spectrum (Nujol): 3200 (broad), 1770, 1660 cm$^{-1}$.

NMR Spectrum (D$_2$O-N$_a$HCO$_3$, $\delta$): 7.12, (1H, s), 5.65 (1H, d, J=5 Hz), 5.10, (1H, d, J=5 Hz), 4.5–5.0, (2H, m), 4.0, (3H, s), 3.5–4.2 (4H, m).

EXAMPLE 7

To a suspension of 2-trifluoroacetamidothiazol-4-ylacetic acid (2.5 g.) in dried methylene chloride (60 ml.) was added phosphorus pentachloride (4.2 g.) under ice-cooling and stirring, and the mixture was further stirred for 2 hours. The precipitated solid was collected by filtration, washed with n-hexane and dried. Thus obtained solid (1.8 g.) was added to a solution of 3-acetoxy-methyl-7-amino-3-cephem-4-carboxylic acid (2.7 g.) and bis(trimethyl-silyl)acetamide (6.1 g.) in dried methylene chloride (80 ml.) at $-25°$ C. with stirring, and the mixture was further stirred for 2 hours at $-20°$ to $0°$ C. and overnight at $0°$ C. to room temperature. After the reaction, methylene chloride was distilled off. To the residue were added water and ethyl acetate, and the mixture was well shaken and then ethyl acetate layer was separated. The ethyl acetate layer was washed with a sodium chloride aqueous solution, dried over magnesium sulfate, and then the solvent was distilled off. The residue was pulverized in diethyl ether. The resulting powder was collected by filtration and dried to give pale yellowish powder of 3-acetoxymethyl-7-(2-trifluoroacetamido-thiazol-4-yl)acetamido-3-cephem-4-carboxylic acid (1.42 g.).

IR Spectrum (Nujol): 3260, 1780, 1725, 1670 cm$^{-1}$.

NMR Spectrum (D$_2$O-N$_a$HCO$_3$, $\delta$): 6.86, (1H, s), 5.61, (1H, d, J=5 Hz), 5.05, (1H, d, J=5 Hz), 4.76, (2H, d, J=3 Hz), 3.70, (2H, s), 3.45, (2H, ABq, J=17 Hz), 2.08, (3H, s).

EXAMPLE 8

To a suspension of 2-trifluoroacetamidothiazol-4-ylacetic acid (2.1 g.) in dried methylene chloride (70 ml.) was added phosphorus pentachloride (3.44 g.) under ice-cooling and stirring, and the mixture was stirred for 2 hours at the same temperature. The precipitated solid was collected by filtration, washed with n-hexane and dried. Thus obtained solid (1.6 g.) was added to a solution of 3-(1-methyl-1H-tetrazol-5-yl)thiomethyl-7-amino-3-cephem-4-carboxylic acid (2.7 g.) and bis(-trimethylsilyl)acetamide (5.0 g.) in dried ethyl acetate (50 ml.) at $-25°$ C. with stirring, and the mixture was further stirred for 1.5 hours at $-10°$ C., for 1 hour at $-10°$ to $0°$ C. and overnight at $0°$ C. to room temperature, respectively. After the reaction, to the reaction mixture was added water and the reaction mixture was stirred, and insoluble substances were filtered off. The ethyl acetate layer was separated from the filtrate, and the remaining aqueous layer was extracted with ethyl acetate. The ethyl acetate layers were combined together and washed with a sodium chloride aqueous solution, dried over magnesium sulfate, and then the solvent was distilled off. The residue was pulverized in diethyl ether. The resulting powder was collected by filtration and dried to give pale yellowish powder of 3-(1-methyl-1H-tetrazol-5-yl)thiomethyl-7-(2-trifluoroacetamidothiazol-4-yl)acetamido-3-cephem-4-carboxylic acid (2.0 g.).

IR Spectrum (Nujol): 3260, 1780, 1725, 1670 cm$^{-1}$.

NMR Spectrum (D$_2$O-N$_a$HCO$_3$, $\delta$): 6.95, (1H, s), 5.64, (1H, d, J=5 Hz), 5.08, (1H, d, J=5 Hz), 4.18, (2H, ABq, J=13 Hz), 4.00, (3H, s), 3.76, (2H, s), 3.56, (2H, Abq, J=17 Hz).

EXAMPLE 9

To a suspension of 2-aminothiazol-4-ylacetic acid (1.78 g.) in dried methylene chloride was introduced dried hydrogen chloride gas for 20 minutes under ice-cooling and stirring, and to the mixture was added phosphorus pentachloride (5.86 g.). The mixture was stirred for 20 minutes at room temperature, and the solvent was distilled off. The residue was dissolved in dried acetone (20 ml.), and the solution was dropwise added to a mixture of 3-(5-acetamido-methyl-1,3,4-thiadiazol-2-yl)thiomethyl-7-amino-3-cephem-4-carboxylic acid (3.0 g.), acetone (15 ml.) and water (15 ml.) under ice-cooling and stirring while the mixture was kept to pH 7.3 to 7.5 with sodium bicarbonate. The mixture was further stirred for 20 minutes at about the same pH and temperature. After the reaction, acetone was distilled off from the reaction mixture. To the residue was added water (50 ml.), and the mixture was adjusted to pH 2. The precipitates were collected by filtration and dissolved in a mixture of acetone (100 ml.) and water (100 ml.) with stirring. The solution was filtered, and the filtrate was concentrated till the total volume became 60 to 70 ml., and then the precipitates were collected by filtration and dried to give light brown powder of 3-(5-acetamidomethyl-1,3,4-thiadiazol-2-yl)thiomethyl-7-(2-aminothiazol-4-yl)acetamido-3-cephem-4-carboxylic acid (1.2 g.).

IR Spectrum (Nujol): 3300(broad), 1770, 1650 cm$^{-1}$.

NMR Spectrum (D$_2$O-N$_a$HCO$_3$, $\delta$): 6.59, (1H, s), 5.78, (1H, d, J=5 Hz), 5.00, (1H, d, J=5 Hz), 4.25, (2H, q, J=14 Hz), 3.80 (2H, q, J=18 Hz), 3.68, (2H, s), 2.09, (3H, s).

EXAMPLE 10

To a mixture of 2-methanesulfonamidothiazol-5-ylacetic acid (1.65 g.), dried methylene chloride (40 ml.) and diethyl ether (4 ml.) was added phosphorus pentachloride (3.5 g.) under ice-cooling and stirring and the mixture was stirred for 30 minutes at the same temperature. To the mixture was added n-hexane, and the precipitated crystals were washed by decantation three times. Thus obtained crystals were gradually added to a solution, which is prepared by adding sodium bicarbonate (2.15 g.) to a suspension of 3-(1-methyl-1H-tetrazol-5-yl)thiomethyl-7-amino-3-cephem-4-carboxylic acid (2.1 g.) in a mixture of acetone (25 ml.) and water (25 ml.) and then by cooling it at $0°$ to $5°$ C., under ice-cooling and stirring while the mixture was kept to pH 7.5 to 8 with a saturated sodium bicarbonate aqueous solution. The mixture was further stirred for 40 minutes at about the same pH and temperature. After the reaction, acetone was removed by washing the reaction mixture with benzene. The aqueous layer was adjusted to pH 5 with 5% hydrochloric acid and filtered. To the aqueous filtrate was overlayed ethyl acetate, and the mixture was gradually adjusted to pH 2 with 5% hydrochloric acid under ice-cooling. The ethyl acetate layer was separated from the mixture, and the remaining aqueous layer was extracted twice with ethyl acetate (70 ml.). The ethyl acetate layers were combined together, washed with water and a saturated sodium chloride aqueous solution in turn and then dried over magnesium sulfate. The solvent was distilled off from the ethyl acetate layer, and the resulting yellow powder was dried to give a mixture (1.6 g.) of 3-(1-methyl-1H-tetrazol-5-yl)thiomethyl-7-(2-methanesulfonamidothiazol-5-yl)acetamido-3-cephem-4-carboxylic acid (hereinafter referred to Amino compound) and 3-(1-methyl-1H-tetrazol-5-yl)thiomethyl-7-(2-methanesulfonimido-2,3-dihydrothiazol-5-yl)acetamido-3-cephem-4-carboxylic acid (hereinafter referred to Imino compound).

IR Spectrum (Nujol): 3300 (broad), 1770, 1710, 1650 cm$^{-1}$.

Thin Layer chromatography (n-butyl acetate:n-butanol:acetic acid:water=80:15:40:24).

Rf value: 0.23 (Imino compound).
Rf value: 0.16 (Amino compound).
NMR Spectrum (D$_2$O-N$_a$HCO$_3$, δ):

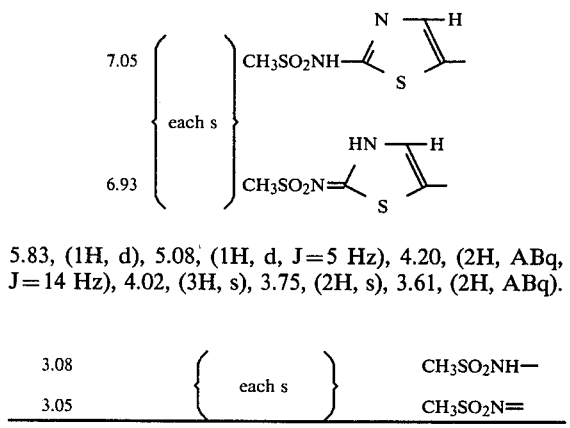

5.83, (1H, d), 5.08, (1H, d, J=5 Hz), 4.20, (2H, ABq, J=14 Hz), 4.02, (3H, s), 3.75, (2H, s), 3.61, (2H, ABq).

| 3.08 | each s | CH$_3$SO$_2$NH— |
| 3.05 | | CH$_3$SO$_2$N= |

EXAMPLE 11

To a suspension of 2-methanesulfonamidothiazol-4-ylacetic acid (1.5 g.) in dried methylene chloride (40 ml.) was added phosphorus pentachloride (2.6 g.) under ice-cooling and stirring, and the mixture was stirred for 5 hours at the same temperature. The precipitated solid was collected by filtration, washed with n-hexane and dried to produce white solid (1.6 g.). The solid was added to a solution of 3-(1-methyl-1H-tetrazol-5-yl)-thiomethyl-7-amino-3-cephem-4-carboxylic acid (2.1 g.) and bis-(trimethylsilyl)acetamide (3.9 g.) in dried methylene chloride (50 ml.) at −20° C. with stirring, and the mixture was further stirred for 1.5 hours at −20° to 0° C. and overnight at room temperature. After the reaction, methylene chloride was distilled off, and to the residue was added water and ethyl acetate. The insoluble solid was collected by filtration, dissolved in acetone (400 ml.) and filtered. The filtrate was concentrated till the total volume of the filtrate became 20 to 30 ml., and diethyl ether was added thereto. The precipitated solid was collected by filtration and dried to give slightly pale yellowish powder of 3-(1-methyl-1H-tetrazol-5-yl)thiomethyl-7-(2-methanesulfonamidothiazol-4-yl)acetamido-3-cephem-4-carboxylic acid (2.2 g.).

IR Spectrum (Nujol): 3300, 1775, 1705, 1664 cm$^{-1}$.

NMR Spectrum (D$_2$o-N$_a$HCO$_3$, δ): 6.57, (1H, s), 5.60, (1H, d, J=5 Hz), 5.05, (1H, d, J=5 Hz), 4.17, (2H, ABq, J=14 Hz), 4.02, (3H, s),
3.61, (2H, s), 3.58, (2H, ABq, J=17 Hz), 3.02, (3H, s).

EXAMPLE 12

To a mixture of 2-methanesulfonamidothiazol-5-ylacetic acid (1.65 g.) and dried methylene chloride (40 ml.) was added phosphorus pentachloride under ice-cooling and stirring, and the mixture was further stirred for 20 minutes at the similar temperature. To the mixture was added diethyl ether (4 ml.) with stirring, and the mixture was further stirred for 30 minutes. To the mixture was added n-hexane, and the precipitated crystals were washed by decantation three times. Thus obtained crystals were gradually added to a solution of 3-(1-methyl-1H-tetrazol-5-yl)-thiomethyl-7-amino-3-cephem-4-carboxylic acid (2.1 g.) and bis-(trimethylsilyl)acetamide (3.9 g.) in dried methylene chloride (50 ml.) at −25° C. with stirring, and the mixture was further stirred for 1 hour at the similar temperature. After the reaction, the solvent was distilled off under reduced pressure. To the residue was added a mixture of ice-water (30 ml.) and ethyl acetate (50 ml.) and the mixture was stirred. The insoluble solid was collected by filtration, dissolved in acetone (200 ml.) and filtered. After treating the filtrate with activated carbon, the solvent was distilled off. The resulting oil was pulverized in ethyl acetate, collected by filtration and then dried to give pale yellow powder of 3-(1-methyl-1H-tetrazol-5-yl)thiomethyl-7-(2-methanesulfonamidothiazol-5-yl)acetamido-3-cephem-4-carboxylic acid (1.8 g.).

IR Spectrum (Nujol): 3300 (broad), 1770, 1710, 1650 cm$^{-1}$.

NMR Spectrum (D$_2$O-N$_a$HCO$_3$, δ): 7.07, (1H, s), 5.62, (1H, d, J=5 Hz), 5.10, (1H, d, J=5 Hz), 4.23, (2H, ABq, J=14 Hz), 4.05, (3H, s), 3.80, (2H, s), 3.62, (2H, ABq, J=18 Hz), 3.10, (3H, s).

EXAMPLE 13

After dropwise addition of phosphorus oxychloride (2.2 g.) to dimethylformamide (0.9 g.) under ice-cooling and stirring, the mixture was stirred for 1 hour at 40° C. To the mixture was added dried methylene chloride (30 ml.), and then the solvent was distilled off. The residue was suspended in ethyl acetate (20 ml.), and to the suspension was added 2-bromothiazol-4-ylacetic acid (2.64 g.) under ice-cooling and stirring, and the mixture became a solution. The solution was cooled at −20° C. and then added to a solution prepared by dropwise addition of bis(trimethylsilyl)acetamide (5.1 g.) to a suspension of 3-(1-methyl-1H-tetrazol-5-yl)-thiomethyl-7-amino-3-cephem-4-carboxylic acid (3.28 g.) in ethyl acetate (50 ml.) and by cooling it to at −20° C. The mixture was stirred for 2 hours at −20° to −10° C. The mixture cooled to at −20° C. and then water (50 ml.) was added thereto. The mixture was extracted with ethyl acetate, and the extract was washed with water and a saturated sodium chloride aqueous solution in turn, and dried over magnesium sulfate. The solvent was distilled off under reduced pressure from the extract and the remaining solid was dried under reduced pressure to give 3-(1-methyl-1H-tetrazol-5-yl)thiomethyl-7-(2-bromothiazol-4-yl)acetamido-3-cephem-4-carboxylic acid (1.7 g.).

IR Spectrum (Nujol): 3300, 1780, 1720, 1680 cm$^{-1}$.

NMR Spectrum (D$_2$O-N$_a$HCO$_3$, δ): 7.40, (1H, s), 5.65, (1H, d, J=5 Hz), 5.06, (1H, d, J=5 Hz), 4.23, (2H, ABq, J=13 Hz), 4.01, (3H, s), 3.85, (2H, s), 3.58, (2H, ABq, J=17 Hz).

EXAMPLE 14

To a suspension of 2-benzenesulfonamidothiazol-4-ylacetic acid (3.3 g.) in dried methylene chloride (50 ml.) was added phosphorus pentachloride (5.0 g.) under ice-cooling and stirring, and the mixture was further stirred at the same temperature till the original crystals' form changed into other form and the crystals were partially dissolved. The mixture was further stirred at the same temperature to produce crystals which were collected by filtration. The crystals were added to a solution prepared by addition of bis(trimethylsilyl)acetamide (6.1 g.) to a suspension of 3-(1-methyl-1H-tetrazol-5-yl)thiomethyl-7-amino-3-cephem-4-carboxylic acid (3.28 g.) in dried methylene chloride (70 ml.) and by cooling it to at −20° C. The mixture was stirred for 3 hours at −20° to 0° C. and further stirred for 2 hours at room temperature and then allowed to stand overnight. After the reaction, the reaction mixture was cooled to at −20° C. To the mixture was added water (50 ml.), and the precipitated brown tar substance was collected and then dissolved in acetone (50 ml.). To the acetone solution was added ethyl acetate (100 ml.), and the ethyl acetate layer was separated. The ethyl acetate layer was treated with activated carbon, and the ethyl acetate was distilled off. The residue was pulverized in diethyl ether, collected by filtration and then dried to give powder of 3-(1-methyl-1H-tetrazol-5-yl)thiomethyl-7-(2-benzenesulfo-namidothiazol-4-yl)acetamido-3-cephem-4-carboxylic acid (2.65 g.).

IR Spectrum (Nujol): 3200, 1780, 1650 cm$^{-1}$.

NMR Spectrum (D$_2$O-N$_a$HCO$_3$, δ): 7.80, (2H, broad), 7.40, (3H, broad), 6.40, (1H, s), 5.60, (1H, d, J=5 Hz), 5.00, (1H, d, J=5 Hz), 4.20, (2H, ABq, J=13 Hz), 3.93, (3H, s), 3.55, (2H, s), 3.45, (2H, ABq, J=18 Hz).

EXAMPLE 15

To a mixture of 2-oxo-2,3-dihydrothiazol-4-ylacetic acid (0.4 g.) and N-hydroxysuccinimide (0.3 g.) in tetrahydrofuran (15 ml.) was added N,N'-dicyclohexylcarbodiimide (0.52 g.) with stirring at room temperature, and the mixture was further stirred for 2 hours at the same temperature. Thus obtained solution was added to a solution of 3-carbamoyloxymethyl-7-amino-3-cephem-4-carboxylic acid (0.816 g.) and trimethylsilylacetamide (0.27 g.) in ethyl acetate (30 ml.) at room temperature, and the mixture was stirred for 16 hours at the same temperature. After the reaction, the reaction mixture was cooled to at −20° C., and then water (20 ml.) was added thereto. After stirring the mixture sufficiently, the mixture was filtered, and then the ethyl acetate layer was separated therefrom. The ethyl acetate layer was washed with a saturated aqueous solution of sodium chloride, dried over magnesium sulfate, treated with activated carbon, and then the solvent was distilled off under reduced pressure. The residue was pulverized in diethyl ether, collected by filtration and then dried to give 3-carbamoyloxymethyl-7-(2-oxo-2,3-dihydrothiazol-4-yl)acetamido-3-cephem-4-carboxylic acid (60 mg.).

IR Spectrum (Nujol): 3300 (broad), 1780, 1720, 1650 cm$^{-1}$.

NMR Spectrum (d$_6$-dimethylsulfoxide, δ): 11.15, (1H, s), 8.93, (1H, d, J=8 Hz), 6.55, (2H, s), 6.05, (1H, s), 5.70, (1H, d,d, J=5 and 8 Hz), 5.10 (1H, d, J=5 Hz), 4.77, (2H, ABq, J=14 Hz), 3.52, (2H, ABq, J=18 Hz), 3.30, (2H, s).

EXAMPLE 16

To a mixture of 2-(3-methylureido)thiazol-4-ylacetic acid (3.23 g.) in dried methylene chloride (50 ml.) was dropwise added a solution of phosphorus pentachloride in dried methylene chloride (80 ml.) with stirring under ice-cooling, and the mixture was stirred for 3 hours under ice-cooling. The precipitates were collected by filtration and washed with n-hexane. Thus obtained precipitates were added to a solution which was prepared by stirring a mixture of 3-(1-methyl-1H-tetrazol-5-yl)thiomethyl-7-amino-3-cephem-4-carboxylic acid (4.95 g.) and trimethylsilylacetamide (11.8 g.) in dried ethyl acetate (75 ml.) for 10 minutes at 40° C. and then by cooling it to at −20° C. The mixture was stirred for 1 hour at −20° to −10° C. and further stirred for 1 hour at −10° to 0° C. The mixture was cooled to at −20° C., and 10% aqueous solution of sodium chloride (7 ml.) was added therto, and then the mixture stirred for 10 minutes at room temperature. After the reaction, ethyl acetate layer was separated out, and the remaining precipitates were washed with ethyl acetate (50 ml.). To the precipitates was added water (30 ml.) and adjusted to pH 5 to 6 with sodium bicarbonate powder with stirring under ice-cooling. Thus obtained solution was subjected to alumina column chromatography, and the eluate was adjusted pH 2 with 17.5% hydrochloric acid. The precipitates were collected by filtration and dried over phosphorus pentachloride under reduced pressure to give white powder of 3-(1-methyl-1H-tetrazol-5-yl)thiomethyl-7-[2-(3-methylureido)thiazol-4-yl]acetamido-3-cephem-4-carboxylic acid (3.20 g.)

IR Spectrum (Nujol): 3500, 3400, 3360, 1770, 1700, 1660, 1550, 1410, 1355, 1250, 1170, 1095, 1065 cm$^{-1}$.

NMR Spectrum (d$_6$-dimethylsulfoxide, δ): 8.90, (1H, d, J=8 Hz), 6.70, (1H, s), 6.43, (1H, broad q, J=4 Hz), 5.70, (1H, d,d, J=5 and 8 Hz), 5.10, (1H, d, J=5 Hz), 4.33, (2H, s), 3.95, (3H, s), 3.70, (2H, s), 3.53, (2H, s), 2.70, (3H, d, J=4 Hz).

EXAMPLE 17

2-Ureidothiazol-4-ylacetic acid (2.01 g.), phosphorus pentachloride (4.17 g.) and 3-(1-methyl-1H-tetrazol-5-yl)thiomethyl-7-amino-3-cephem-4-carboxylic acid (3.30 g.) were treated in the similar manner to that of Example 16 to give 3-(1-methyl-1H-tetrazol-5-yl)-thiomethyl-7-(2-ureidothiazol-4-yl)acetamido-3-cephem-4-carboxylic acid (0.7 g.).

IR Spectrum (Nujol): 3450, 3350, 3200, 1775, 1690, 1550, 1400, 1360, 1240, 1175, 1100, 1060 cm$^{-1}$.

NMR Spectrum (d$_6$-dimethylsulfoxide, δ): 9.28, (1H, d, J=8 Hz), 6.70, (1H, s), 6.40, (1H, s), 5.6, (2H, broad), 5.73, (1H, d,d, J=5 and 8 Hz), 5.08, (1H, d, J=5 Hz), 4.48, (2H, s), 3.93, (3H, s), 3.70, (2H, s), 3.53, (2H, s).

EXAMPLE 18

2-Methanesulfonamidothiazol-4-ylacetic acid (1.13 g.), 3-carbamoyloxymethyl-7-amino-3-cephem-4-carboxylic acid (1.37 g.), phosphorus pentachloride (2.08 g.) and trimethylsilylacetamide (4.58 g.) were treated in the similar manner to that of Example 12 to give 3-carbamoyloxymethyl-7-(2-methanesulfonamidothiazol-4-yl)-acetamido-3-cephem-4-carboxylic acid (1.79 g.)

IR Spectrum (Nujol): 3450, 3300, 1770, 1710, 1660 cm$^{-1}$.

NMR Spectrum (d$_6$-dimethylsulfoxide, δ): 9.1, (1H, d, J=8 Hz), 6.6, (2H, s), 6.57, (1H, s), 5.75, (1H, d,d, J=5 and 8 Hz), 5.1, (1H, d), 4.8, (2H, ABq, J=15 Hz), 3.58, (4H, broad s), 2.9, (3H, s).

The following compounds were obtained by using the similar procedures to those of the above examples.

(1) 3-(1-methyl-1H-tetrazol-5-yl)thiomethyl-7-(2-aminothiazol-4-yl)methylthioacetamido-3-cephem-4-carboxylic acid (powder), mp 180° to 250° C. (dec.)

IR Spectrum (Nujol): 3100-3300 (NH), 1765 (CO) cm$^{-1}$.

(2) 3-(1-methyl-1H-tetrazol-5-yl)thiomethyl-7-(6-aminopyridazin-3-yl)thioacetamido-3-cephem-4-carboxylic acid (powder), mp 142° to 159° C. (dec.)

IR Spectrum (Nujol): 1760 (CO), 1690-1630 (CO) cm$^{-1}$.

(3) 3-(1-methyl-1H-tetrazol-5-yl)thiomethyl-7-(4-amino-6-hydroxy-pyrimidin-2-yl)thioacetamido-3-cephem-4-carboxylic acid (Powder), mp 190° to 200° C. (dec.)

IR Spectrum (Nujol): 3200-3500 (NH, OH), 1780 (CO) cm$^{-1}$.

(4) 3-(1-methyl-1H-tetrazol-5-yl)thiomethyl-7-(2-methanesulfonamido-thiazol-5-yl)thioacetamido-3-cephem-4-carboxylic acid (Powder), mp 95° to 115° C. (dec.):

IR Spectrum (Nujol): 1780 (CO), 1720-1660 (CO) cm$^{-1}$.

(5) 3-(1-methyl-1H-tetrazol-5-yl)thiomethyl-7-(5-methanesulfonamido-1,3,4-thiadiazol-2-yl)thioacetamido-3-cephem-4-carboxylic acid (Powder), dp 210° C.

IR Spectrum (Nujol): 1775 (CO), 1720 (CO), 1670 (CO) cm$^{-1}$.

(6) 3-(5-methyl-1,3,4-thiadiazol-2-yl)thiomethyl-7-(5-amino-1,3,4-thiadiazol-2-yl)thioacetamido-3-cephem-4-carboxylic acid (Powder), mp 130° to 133° C. (dec.)

(7) 3-(1-methyl-1H-tetrazol-5-yl)thiomethyl-7-(5-amino-2H-tetrazol-2-yl)acetamido-3-cephem-4-carboxylic acid, mp 98° to 100° C. (dec.)

(8) 3-(5-methyl-1,3,4-thiadiazol-2-yl)thiomethyl-7-(5-aminomethyl-1,3,4-thiadiazol-2-yl)thioacetamido-3-cephem-4-carboxylic acid (Powder), mp 132° to 140° C. (dec.)

(9) 3-(5-methyl-1,3,4-thiadiazol-2-yl)thiomethyl-7-(5-t-butoxy-carbonylaminomethyl-1,3,4-thiadiazol-2-yl)thioacetamido-3-cephem-4-carboxylic acid (Powder), mp 95° to 102° C. (dec.)

(10) 3-carbamoyloxymethyl-7-(2-aminothiazol-4-yl)acetamido-3-cephem-4-carboxylic acid.

IR Spectrum (Nujol): 3450, 3300, 1780, 1690, 1660 cm$^{-1}$.

EXAMPLE 19

A solution of 3-acetoxymethyl-7-(2-aminothiazol-5-yl)acetamido-3-cephem-4-carboxylic acid (2 g.) and potassium 1-methyl-1H-tetrazole-5-thiolate (0.7 g.) in pH 6.4 phosphate buffer (50 ml.) was stirred for 4 hours with continuous introduction of nitrogen gas while the reaction mixture was kept to pH 6.4 to 7 with sodium bicarbonate. After the reaction, the reaction mixture was cooled and then filtered. The filtrate was adjusted to pH 2.5 with diluted hydrochloric acid under ice-cooling, and the precipitates were collected by filtration and then purified similarly as that of Example 6 to give light brown powder of 3-(1-methyl-1H-tetrazol-5-yl)thiomethyl-7-(2-aminothiazol-5-yl)acetamido-3-cephem-4-carboxylic acid (1.05 g.).

IR Spectrum (Nujol): 3200 (broad), 1770, 1660 cm$^{-1}$.

The following compounds were obtained by using the similar procedure to that of the above Example 19.

(1) 3-(benzimidazol-2-yl)thiomethyl-7-(2-aminothiazol-4-yl)acetamido-3-cephem-4-carboxylic acid (Pale yellow powder)

IR Spectrum (Nujol): 3100-3500, 1775, 1665 cm$^{-1}$.

(2) 3-(1-allyl-1H-tetrazol-5-yl)thiomethyl-7-(2-aminothiazol-4-yl)acetamido-3-cephem-4-carboxylic acid (Pale Yellow powder)

IR Spectrum (Nujol): 3200-3500, 1775, 1670 cm$^{-1}$.

(3) 3-(1-methyl-1H-tetrazol-5-yl)thiomethyl-7-(2-amino-4-methyl-thiazol-5-yl)acetamido-3-cephem-4-carboxylic acid (Yellowish brown powder)

IR Spectrum (Nujol): 3200-3500, 1770, 1670 cm$^{-1}$.

(4) 3-(5-methyl-1,3,4-thiadiazol-2-yl)thiomethyl-7-(2-trifluoroacetamidothiazol-4-yl)acetamido-3-cephem-4-carboxylic acid (White powder)

IR Spectrum (Nujol): 3150-3300, 1780, 1720, 1670 cm$^{-1}$.

(5) 3-(5-methyl-1,3,4-thiadiazol-2-yl)thiomethyl-7-(2-amino-4-methylthiazol-5-yl)acetamido-3-cephem-4-carboxylic acid (Yellowish brown powder)

IR Spectrum (Nujol): 3200-3500, 1770, 1645 cm$^{-1}$.

(6) 3-(1-methyl-1H-tetrazol-5-yl)thiomethyl-7-(2-trifluoroacetamido-thiazol-4-yl)acetamido-3-cephem-4-carboxylic acid IR Spectrum (Nujol): 3260, 1780, 1725, 1670 cm$^{-1}$.

(7) 3-(5-acetamidomethyl-1,3,4-thiadiazol-2-yl)thiomethyl-7-(2-aminothiazol-4-yl)acetamido-3-cephem-4-carboxylic acid IR Spectrum (Nujol): 3300 (broad), 1770, 1650 cm$^{-1}$.

(8) 3-(1-methyl-1H-tetrazol-5-yl)thiomethyl-7-(2-methanesulfonamido-thiazol-4-yl)acetamido-3-cephem-4-carboxylic acid IR Spectrum (Nujol): 3300, 1775, 1705, 1664 cm$^{-1}$.

(9) 3-(1-methyl-1H-tetrazol-5-yl)thiomethyl-7-(2-methanesulfonamido-thiazol-5-yl)acetamido-3-cephem-4-carboxylic acid IR Spectrum (Nujol): 3300 (broad), 1770, 1710, 1650 cm$^{-1}$.

(10) 3-(1-methyl-1H-tetrazol-5-yl)thiomethyl-7-(2-bromothiazol-4-yl)acetamido-3-cephem-4-carboxylic acid IR Spectrum (Nujol): 3300, 1780, 1720, 1680 cm$^{-1}$.

(11) 3-(1-methyl-1H-tetrazol-5-yl)thiomethyl-7-(2-benzenesulfonamido-thiazol-4-yl)acetamido-3-cephem-4-carboxylic acid IR Spectrum (Nujol): 3200, 1780, 1650 cm$^{-1}$.

(12) 3-(1-methyl-1H-tetrazol-5-yl)thiomethyl-7-(2-aminothiazol-4-yl)methylthioacetamido-3-cephem-4-carboxylic acid (Powder), mp 180° to 250° C. (dec.)

IR Spectrum (Nujol): 3100-3300 (NH), 1765 (CO) cm$^{-1}$.

(13) 3-(1-methyl-1H-tetrazol-5-yl)thiomethyl-7-(6-aminopyridazin-3-yl)thioacetamido-3-cephem-4-carboxylic acid (Powder), mp 142° to 159° C. (dec.)

IR Spectrum (Nujol): 1760 (CO), 1690-1630 (CO) cm$^{-1}$.

(14) 3-(1-methyl-1H-tetrazol-5-yl)thiomethyl-7-(4-amino-6-hydroxy-pyrimidin-2-yl)thioacetamido-3- cephem-4-carboxylic acid (Powder), mp 190° to 200° C. (dec.)

IR Spectrum (Nujol) 3200–3500 (NH, OH), 1780 (CO) cm$^{-1}$.

(15) 3-(1-methyl-1H-tetrazol-5-yl)thiomethyl-7-(2-methanesulfonamido-thiazol-5-yl)thioacetamido-3-cephem-4-carboxylic acid (Powder), mp 95° to 115° C. (dec.)

IR Spectrum (Nujol): 1780 (CO), 1720-1660 (CO) cm$^{-1}$.

(16) 3-(1-methyl-1H-tetrazol-5-yl)thiomethyl-7-(5-methanesulfonamido-1,3,4-thiadiazol-2-yl)thioacetamido-3-cephem-4-carboxylic acid (Powder), dp 210° C.

(17) 3-(5-methyl-1,3,4-thiadiazol-2-yl)thiomethyl-7-(5-aminomethyl-1,3,4-thiadiazol-2-yl)thioacetamido-3-cephem-4-carboxylic acid (Powder), mp 132° to 140° C. (dec.)

(18) 3-(5-methyl-1,3,4-thiadiazol-2-yl)thiomethyl-7-(5-amino-1,3,4-thiadiazol-2-yl)thioacetamido-3-cephem-4-carboxylic acid (Powder), mp 130° to 133° C. (dec.)

(19) 3-(1-methyl-1H-tetrazol-5-yl)thiomethyl-7-(5-amino-2H-tetrazol-2-yl)acetamido-3-cephem-4-carboxylic acid, mp 98° to 100° C. (dec.)

(20) 3-(5-methyl-1,3,4-thiadiazol-2-yl)thiomethyl-7-(5-t-butoxycarbonylaminomethyl-1,3,4-thiadiazol-2-yl)thioacetamido-3-cephem-4-carboxylic acid (Powder), mp 95° to 102° C. (dec.)

EXAMPLE 20

A mixture of 2-(2-aminothiazol-4-ylmethyl)isothiourea (1.57 g.) and 1 N sodium hydroxide (24 ml.) was stirred for 15 minutes at room temperature, and then the mixture was adjusted to pH 9 with 1 N hydrochloric acid (12 ml.). Thus obtained solution containing 2-aminothiazol-4-ylmethanethiol was dropwise added to a mixture of 3-(1-methyl-1H-tetrazol-5-yl)thiomethyl-7-bromoacetamido-3-cephem-4-carboxylic acid (2.16 g.), sodium bicarbonate (0.67 g.), water (33 ml.) and ethanol (33 ml.) over 15 minutes at room temperature with stirring. The mixture was stirred for 1 hour at room temperature, and it was adjusted to pH 4 with 1 N hydrochloric acid. The mixture was allowed to stand for overnight in a refrigerator, and the precipitates were collected by filtration, washed with a small amount of water and then dried to give powder of 3-(1-methyl-1H-tetrazol-5-yl)thiomethyl-7-(2-aminothiazol-4-yl)methylthioacetamido-3-cephem-4-carboxylic acid (0.7 g.), mp 180° to 250° C. (dec.)

IR Spectrum (Nujol): 3100–3300 (NH), 1765 (CO) cm$^{-1}$.

NMR Spectrum (D$_3$CSOCD$_3$, δ): 8.90, (1H, d), 6.29, (1H, s), 5.70, (1H, m), 5.01, (1H, d), 4.30, (2H, m), 3.90, (3H, s), 3.57, (4H, m), 3.20, (2H, m).

EXAMPLE 21

To a mixture of 3-(1-methyl-1H-tetrazol-5-yl)thiomethyl-7-bromoacetamido-3-cephem-4-carboxylic acid (0.45 g.), sodium bicarbonate (0.185 g.), pH 6.4 phosphate buffer (10 ml.) and acetone (5 ml.) was added 2-methanesulfonamidothiazole-5-thiol (0.21 g.) at room temperature with stirring, and the mixture was stirred for 1 hour at the same temperature. After the reaction, to the reaction mixture was added water (10 ml.) and washed with ethyl acetate. The aqueous layer was adjusted to pH 2 to 3 with 1 H hydrochloric acid and then extracted with ethyl acetate. The aqueous layer was salting out and then further extracted with ethyl acetate. The ethyl acetate layers were combined together, washed with a small amount of water and dried over magnesium sulfate. After distillation of ethyl acetate from the ethyl acetate layer, the residue was pulverized in diethyl ether. The pulverized residue was collected by filtration and dried to give powder of 3-(1-methyl-1H-tetrazol-5-yl)thiomethyl-7-(2-methanesulfonamido-thiazol-5-yl)thioacetamido-3-cephem-4-carboxylic acid (0.18 g.), mp 95° to 115° C. (dec.).

IR Spectrum (Nujol): 1780 (CO), 1720-1660 (CO) cm$^{-1}$.

NMR Spectrum (D$_3$CSOCD$_3$, δ): 9.1, (1H, m), 7.37, (1H, s), 5.70, (1H, m), 5.10, (1H, d), 3.4–4.4, (7H, m), 2.92, (3H, s).

The following compounds were obtained by using the similar procedures to those of the above examples 21 and 22.

(1) 3-(1-methyl-1H-tetrazol-5-yl)thiomethyl-7-(5-methanesulfonamido-1,3,4-thadiazol-2-yl)thioacetamido-3-cephem-4-carboxylic acid (Powder), dp 210° C.

(2) 3-(1-methyl-1H-tetrazol-5-yl)thiomethyl-7-(6-aminopyridazin-3-yl)thioacetamido-3-cephem-4-carboxylic acid (Powder), mp 142° to 159° C. (dec.).

(3) 3-(1-methyl-1H-tetrazol-5-yl)thiomethyl-7-(4-amino-6-hydroxy-pyrimidin-2-yl)thioacetamido-3-cephem-4-carboxylic acid (Powder), mp 190° to 200° C. (dec.).

(4) 3-(5-methyl-1,3,4-thiadiazol-2-yl)thiomethyl-7-(5-amino-1,3,4-thiadiazol-2-yl)thioacetamido-3-cephem-4-carboxylic acid (Power), mp 130° to 133° C. (dec.).

(5) 3-(5-methyl-1,3,4-thiadiazol-2-yl)thiomethyl-7-(5-aminomethyl-1,3,4-thiadiazol-2-yl)thioacetamido-3-cephem-4-carboxylic acid (Powder), mp 132° to 140° C. (dec.).

(6) 3-(5-methyl-1,3,4-thiadiazol-2-yl)thiomethyl-7-(5-t-butoxycarbonylaminomethyl-1,3,4-thiadiazol-2-yl)thioacetamido-3-cephem-4-carboxylic acid (Powder), mp 95° to 102° C. (dec.).

EXAMPLE 22

To a solution of sodium bicarbonate (0.067 g.) in pH 6.4 phosphate buffer (5 ml.) was gradually added 3-carbamoyloxymethyl-7-(3-oxo-4-thiocyanatobutyramido)-3-cephem-4-carboxylic acid (0.33 g.) with stirring at room temperature, and then the mixture was allowed to stand for 30 hours at room temperature. After the reaction, to the reaction mixture was added ethyl acetate (50 ml.). The reaction mixture was adjusted to pH 2 with 50% phosphoric acid, and then the ethyl acetate layer was separated therefrom. The remaining aqueous layer was further extracted with ethyl acetate. The ethyl acetate layers were combined together, washed with a saturated aqueous solution of sodium chloride dried over magnesium sulfate, treated with activated carbon and then the solvent was distilled off. The residue was pulverized in diethyl ether, collected by filtration and then dried to give 3-carbamoyloxymethyl-7-(2-oxo-2,3-dihydrothiazol-4-yl)acetamido-3-cephem-4-carboxylic acid (0.1 g.). The IR Spectrum and NMR Spectrum of this object compound were identical as those of the object compound obtained in Example 15.

EXAMPLE 23

To a solution of thiourea (0.103 g.) and sodium bicarbonate (0.11 g.) in a mixture of tetrahydrofuran (1.3 ml.) and water (1.3 ml.) was gradually added 3-carbamoyloxymethyl-7-(3-oxo-4-bromobutyramido)-3- cephem-4-carboxylic acid (0.55 g.) with stirring at room temperature, and then the resulting solution was stirred for 40 minutes at room temperature. After the reaction, the precipitated crystals were collected by filtration with suction, washed with water, tetrahydrofuran and water in turn, and then dried over phosphorus pentoxide to give 3-carbamoyloxymethyl-7-(2-aminothiazol-4-yl)acetamido-3-cephem-4-carboxylic acid (0.48 g.).

IR Spectrum (Nujol): 3450, 3300, 1780, 1690, 1660 cm$^{-1}$.

NMR Spectrum (d$_6$-dimethylsulfoxide, $\delta$): 8.85, (1H, d), 6.89, (2H, s), 6.58, (2H, s), 6.27, (1H, s), 5.68, (1H, d,d, J=5 and 8 Hz), 5.08, (1H, d, J=5 Hz), 4.75, (2H, ABq, J=13 Hz), 3.50, (2H, ABq, J=17 Hz), 3.40, (2H, s).

The following compounds were obtained by using the similar procedure to that of the above Example 23.

(1) 3-(benzimidazol-2-yl)thiomethyl-7-(2-aminothiazol-4-yl)acetamido-3-cephem-4-carboxylic acid IR Spectrum (Nujol): 3100–3500, 1775, 1665 cm$^{-1}$.

(2) 3-(1-allyl-1H-tetrazol-5-yl)thiomethyl-7-(2-aminothiazol-4-yl)acetamido-3-cephem-4-carboxylic acid IR Spectrum (Nujol): 3200–3500, 1775, 1670 cm$^{-1}$.

(3) 3-(5-acetamidomethyl-1,3,4-thiadiazol-2-yl)thiomethyl-7-(2-aminothiazol-4-yl)acetamido-3-cephem-4-carboxylic acid IR Spectrum (Nujol): 3300 (broad), 1770, 1650 cm$^{-1}$.

PREPARATION OF THE STARTING COMPOUNDS (1) 2-Methanesulfonamidothiazol-4-ylacetic acid (a) To a solution of ethyl 2-aminothiazol-4-ylacetate (18.6 g.) in dried methylene chloride (140 ml.) was added pyridine, and to the mixture was dropwise added a solution of mesyl chloride (17.2 g.) in dried methylene chloride (20 ml.) under ice-cooling and stirring. The mixture was further stirred for 5 hours at room temperature, and to the mixture was added a mixture of water and ethyl acetate. After adjusting the mixture to about pH 2 with 10% hydrochloric acid under ice-cooling, the precipitates were collected by filtration, washed with ethyl acetate and dried to give ethyl 2-methanesulfonamidothiazol-4-ylacetate (9.2 g.), mp 207° to 208° C.

IR Spectrum (Nujol): 3100, 1725 cm$^{-1}$. NMR Spectrum (CD$_3$SOCD$_3$, $\delta$): 6.58, (1H, s), 4.13, (2H, q, J=7 Hz), 3.67, (2H, s), 2.90, (3H, s), 1.20, (3H, t, J=7 Hz).

(b) To a solution of potassium hydroxide (2.9 g.) in water (80 ml.) was added ethyl 2-methanesulfonamidothiazol-4-ylacetate (9.1 g.) under ice-cooling and stirring, and the mixture was stirred for 1 hour at room temperature. After the reaction, to the reaction mixture was added a mixture of water and ethyl acetate, and then the aqueous layer was separated. The remaining ethyl acetate layer was extracted twice with 10% hydroxide aqueous solution. The extracts were combined with the above obtained aqueous layer, and the mixture was acidified with hydrochloric acid under ice-cooling. The precipitated crystals were collected by filtration, washed with water and dried to give 2-methanesulfonamidothiazol-4-ylacetic acid (5.94 g.), mp 158°–160° C. (dec.).

IR Spectrum (Nujol): 3200, 1730 cm$^{-1}$.

NMR Spectrum (D$_2$O-NaHCO$_3$, $\delta$): 6.48, (1H, s), 3.47, (2H, s), 3.07, (3H, s).

(2) 2-Methanesulfonamidothiazol-5-ylacetic acid (a) To a solution of ethyl 2-aminothiazol-5-ylacetate (32 g.) in methylene chloride (160 ml.) was added pyridine (27.2 g.) under ice-cooling, and to the mixture was dropwise added mesyl chloride (29.6 g.) in methylene chloride (29.6 ml.) over 30 minutes at 8° to 10° C. The mixture was further stirred for 8 hours at room temperature. After the reaction, methylene chloride was distilled off from the reaction mixture, and to the residue were added water (300 ml.) and ethyl acetate (300 ml.). The resulting mixture was adjusted to pH 2 with 10% hydrochloric acid under ice-cooling, and the precipitates were collected by filtration and washed with ethyl acetate. The precipitates were recrystallized from ethanol (600 ml.) to give ethyl 2-methanesulfonamidothiazol-5-ylacetate (27.3 g.), mp 153° to 155° C.

IR Spectrum (Nujol): 3075 (NH), 1722 (CO) cm$^{-1}$.

NMR Spectrum (CD$_3$SOCD$_3$, $\delta$): 7.46, (1H, s), 4.15, (2H, q, J=8 Hz), 3.80, (2H, s), 3.12, (3H, s), 1.22, (3H, t, J=8 Hz).

The ethanol mother liquor was concentrated to give ethyl 2-methanesulfonimido-2,3-dihydrothiazol-5-ylacetate (3.3 g.), mp 175° to 177° C.

IR Spectrum (Nujol): 3120 (NH), 1724 (CO) cm$^{-1}$.

NMR Spectrum (CD$_3$SOCD$_3$, $\delta$): 6.96, (1H, s), 4.07, (2H, q, J=7 Hz), 3.68, (2H, s), 2.85, (3H, s), 1.18, (3H, t, J=7 Hz).

(b) To a solution of 1 N potassium hydroxide aqueous solution (246 ml.) in ethanol (52 ml.) was added ethyl 2-methanesulfonamidothiazol-5-ylacetate (26 g.) over 1 minutes under ice-cooling and stirring, and the mixture was stirred for about 5 minutes to produce a homogeneous solution. The solution was further stirred for 5 minutes and adjusted to pH 2 with 10% hydrochloric acid under ice-cooling and then stirred for 20 minutes at the same temperature. The precipitated crystals were collected by filtration, air-dried overnight and then dried over phosphorus pentoxide to give colorless crystals of 2-methanesulfonamidothiazol-2-ylacetic acid (16.6 g.), mp 232° to 234° C. (dec.).

IR Spectrum (Nujol): 3150 (NH), 1686 (CO) cm$^{-1}$.

NMR Spectrum (D$_2$O-N$_a$HCO$_3$, $\delta$): 6.96, (1H, t, J=1 Hz), 3.56, (2H, d, J=1 Hz), 3.12, (3H, s).

(3) 2-Trifluoroacetamidothiazol-4-ylacetic acid (a) To a solution of ethyl 2-aminothiazol-4-ylacetate (18.6 g.) in tetrahydrofuran (140 ml.) was added pyridine (11 g.), and to the mixture was dropwise added trifluoroacetic anhydride (23.1 g.) under ice-cooling and stirring. The mixture was further stirred for 2 hours at the same temperature, and then the solvent was distilled off. To the residue was added a mixture of ethyl acetate and water and ethyl acetate layer was separated. The ethyl acetate layer was washed with diluted hydrochloric acid and a sodium chloride aqueous solution in turn. After drying the ethyl acetate layer over magnesium sulfate, ethyl acetate was distilled off. To the remaining pale yellow solid was added n-hexane, and the solid was collected by filtration and dried to give ethyl 2-trifluoroacetamidothiazol-4-ylacetate (23.4 g.), mp 119°–121° C.

IR Spectrum (Nujol): 3200 (NH), 1730 (COOCH$_3$ and COCF$_3$) cm$^{-1}$.

NMR Spectrum (CDCl$_3$, $\delta$): 9.92, (1H, broad s), 6.93, (1H, s), 4.20, (2H, q, J=7 Hz), 3.75, (2H, s), 1.27, (3H, t, J=7 Hz).

(b) To a solution of potassium hydroxide (4.2 g.) in water (100 ml.) was added ethyl 2-trifluoroacetamidothiazol-4-ylacetate (14.1 g.) at room temperature with stirring, and the mixture was stirred for 1 hour at room temperature. After the reaction, the reaction mixture was washed with ethyl acetate and adjusted to about pH 3 with 10% hydrochloric acid under ice-cooling and stirring. The precipitated solid was collected by filtration and dried over phosphorus pentoxide to give 2-trifluoroacetamidothiazol-4-ylacetic acid (8.5 g.), mp 117°-120° C.

IR Spectrum (Nujol): 1720, 1680 cm$^{-1}$.

NMR Spectrum (D$_2$O-NaHCO$_3$, δ): 6.95, (1H, s), 3.66, (2H, s).

(4) 2-Benzenesulfonamidothiazol-4-ylacetic acid (a) To a solution of ethyl 2-aminothiazol-4-ylacetate (18.6 g.) in pyridine (140 ml.) was added benzenesulfonyl chloride (17.7 g.), and the mixture was stirred for 50 minutes at 90° to 100° C., and then pyridine was distilled off under reduced pressure. To the residue was added 10% hydrochloric acid (200 ml.), and then extracted with ethyl acetate (100 ml.). The extract was washed with a saturated sodium chloride aqueous solution (50 ml.×2) and treated with an activated carbon and then dried. After distillation of ethyl acetate from the extract, the precipitated crystals were collected by filtration and washed with diethyl ether and dried to give ethyl 2-benzenesulfonamidothiazol-4-ylacetate (19.0 g.), mp 129° to 130° C.

IR Spectrum (Nujol): 3090, 1730 cm$^{-1}$.

NMR Spectrum (CDCl$_3$, δ): 12.0, (1H, broad), 7.92, (2H, m), 7.50, (3H, m), 6.39, (1H, s), 4.19, (2H, q, J=7 Hz), 3.83, (2H, s), 1.20, (3H, t, J=7 Hz).

(b) To an aqueous solution of potassium hydroxide (5.0 g.) in water (150 ml.) was added ethyl 2-benzenesulfonamidothiazol-4-ylacetate (9.1 g.) at 10° C. with stirring, and the mixture was stirred for 30 minutes at room temperature. The reaction mixture was adjusted to pH 4 to 4.5 with acetic anhydride, and the mixture was stirred under ice-cooling till the crystals precipitated. The crystals were collected by filtration and dried to give 2-benzenesulfonamidothiazol-4-ylacetic acid (7.7 g.), mp 94° to 96° C. (dec.).

IR Spectrum (Nujol): 3050, 1690, 1650 cm$^{-1}$.

NMR Spectrum (D$_2$O-NaHCO$_3$, δ): 7.96, (2H, m), 7.40, (3H, m), 6.33, (1H, s), 3.53, (2H, s).

(5) 2-methanesulfonamidothiazole-5-thiol (a) To a mixture of 2-amino-5-benzylthiothiazole (6.7 g.) and pyridine (50 ml.) was dropwise added mesyl chloride (10.3 g.) over 15 minutes under ice-cooling and stirring, and the mixture was stirred for 3.5 hours at room temperature. After the reaction, the reaction mixture was poured into ice-water (300 ml.), and the precipitates were collected by filtration and then washed with water. The precipitates were added to 1 N sodium hydroxide aqueous solution (50 ml.), and the mixture was heated at 60° C. to produce a solution. The solution was treated with activated carbon and then neutralized. The precipitates were collected by filtration, washed with water and then dried to give powder of 2-methanesulfonamido-5-benzylthiothiazole (7.7 g.), mp 159° to 162° C.

IR Spectrum (Nujol): 1575, 1530, 1300, 1115 cm$^{-1}$.

NMR Spectrum (D$_3$CSOCD$_3$, δ): 7.27, (5H, s), 7.17, (1H, s), 3.99, (2H, s), 2.90, (3H, s).

(b) To a mixture of aluminum chloride (510 mg.) and dried toluene (15 ml.) was added 2-methanesulfonamido-5-benzylthiothiazole (560 mg.) over 5 minutes at 110° C. with stirring, and the mixture was further stirred for 1 hour at the same temperature. After the reaction, toluene was removed by decantation. To the residue was added a mixture of water (20 ml.) and methylene chloride (20 ml), and the mixture was stirred for 30 minutes. Thus obtained insoluble material was collected by filtration, washed with water and then dried to give 2-methanesulfonamidothiazole-5-thiol (120 mg.), mp 185° to 192° C. (dec.).

IR Spectrum (Nujol): 1580, 1530, 1310, 1295, 1120 cm$^{-1}$.

NMR Spectrum (D$_3$CSOCD$_3$, δ): 7.67, (1H, s), 2.97, (3H, s).

(6) 5-methanesulfonamido-1,3,4-thiadiazole-2-thiol

5-Methanesulfonamido-1,3,4-thiadiazole-2-thiol, mp 215° to 217° C. (dec.) was obtained from 2-amino-5-benzylthio-1,3,4,-thiadiazole by using the similar procedures as those of the above preparation methods (5)(a) and (5)(b).

IR Spectrum (Nujol): 3200-3000, 1545, 1150, 1065 cm$^{-1}$.

NMR Spectrum (D$_3$CSOCD$_3$, δ): 10.6-11.4, (1H, broad), 3.26, (3H, s).

(7)
3-Carbamoyloxymethyl-7-(3-oxo-4-bromobutyramido)-3-cephem-4-carboxylic acid

To a solution of 4-methylene-2-oxetanone (0.4 g.) in dried methylene chloride (5 ml.) was dropwise added a solution of bromine (0.75 g.) in dried methylene chloride (5 ml.) under cooling at −30° C., and then the mixed solution was stirred for 15 minutes at −10° to −5° C. Thus obtained solution was dropwise added to a solution of 3-carbamoyloxymethyl-7-amino-3-cephem-4-carboxylic acid (1.1 g.) and trimethylsilylacetamide (6.3 g.) in dried methylene chloride (15 ml.) under cooling at −20° C. The reaction temperature was gradually raised to at room temperature, and then the reaction mixture was stirred for 10 minutes at room temperature. After cooling the reaction mixture to at −20° C., water was added thereto, and then the mixture was stirred. The mixture was added a mixture of water (40 ml.) and ethyl acetate (80 ml.) with stirring, and the mixture was further stirred for 5 minutes, and then ethyl acetate layer was separated therefrom. The ethyl acetate layer was filtered, washed with a saturated aqueous solution of sodium chloride, dried over magnesium sulfate and then treated with activated carbon. After distillation of the solvent from the ethyl acetate layer, the residue was pulverized in diethyl ether, collected by filtration and then dried to give 3-carbamoyloxymethyl-7-(3-oxo-4-bromobutyramido)-3-cephem-4-carboxylic acid (1.02 g.)

IR Spectrum (Nujol): 3500-3300 (broad), 1775, 1720, 1670 cm$^{-1}$.

NMR Spectrum (d$_6$-dimethylsulfoxide, δ): 9.05, (1H, d, J=8 Hz), 6.61, (2H, s), 5.70, (1H, d,d, J=5 and 8 Hz), 5.10, (1H, d, J=5 Hz), 4.68, (2H, Abq, J=14 Hz), 4.41, (2H, s), 3.62, (2H, s), 3.60, (2H, ABq, J=18 Hz).

(8)
3-Carbamoyloxymethyl-7-(3-oxo-4-thiocyanatobutyramido)-3-cephem-4-carboxylic acid A mixture of 3-carbamoyloxymethyl-7-(3-oxo-4-bromobutyramido)-3-cephem-4-carboxylic acid (0.52 g.) and potassium thiocyanate (0.174 g.) in acetonitrile (10 ml.) was stirred for 6 hours at room temperature, and then acetonitrile was distilled off therefrom. To the residue were added ethyl acetate (50 ml.) and a saturated aqueous solution of sodium chloride (20 ml.), and the mixture was adjusted to pH 2 with 50% phosphoric acid with stirring, and then ethyl acetate layer was separated therefrom. The remaining aqueous layer was further extracted with ethyl acetate. The ethyl acetate layers were combined together, dried over magnesium sulfate, treated with activated carbon, and then the solvent was distilled off therefrom. The residue was pulverized in diethyl ether, collected by filtration and then dried to give 3-carbamoyloxymethyl-7-(3-oxo-4-thiocyanatobutyramido)-3-cephem-4-carboxylic acid (0.36 g.).

IR Spectrum (Nujol): 3300 (broad), 1780, 1720, 1650 cm$^{-1}$.

NMR Spectrum (d$_6$-dimethylsulfoxide, δ): 9.10, (1H, d, J=8 Hz), 6.52, (2H, s), 5.63, (1H, d,d, J=5 and 8 Hz), 5.05, (1H, d, J=5 Hz), 4.35, (2H, s), 3.70, (2H, ABq, J=14 Hz), 3.55, (2H, ABq, J=18 Hz), 3.51, (2H, s).

(9) 2-(3-Methylureido)thiazol-4-ylacetic acid (a) To a solution of ethyl 2-aminothiazol-4-ylacetate (27.4 g.) in dimethylsulfoxide (135 ml.) was dropwise added methylisocyanate (13.05 g.) with stirring at room temperature, and the mixture was stirred for 3 hours at 40° C. After the reaction, the reaction mixture was poured into water (500 ml.), and then extracted with ethyl acetate. The extract was washed with water and a saturated aqueous solution of sodium chloride in turn and then dried over magnesium sulfate. After distillation of the solvent from the extract, the residue was pulverized in diethyl ether, collected by filtration and then dried to give colorless crystals of ethyl 2-(3-methylureido)thiazol-4-ylacetate (25.7 g.), mp 158° to 159° C.

IR Spectrum (Nujol): 3400, 3200, 3100, 1730, 1680, 1655 cm$^{-1}$.

(b) To a solution of ethyl 2-(3-methylureido)thiazol-4-ylacetate (12.8 g.) in a mixture of methanol (240 ml.) and water (240 ml.) was dropwise added 1 N potassium hydroxide aqueous solution (52.7 ml.) with stirring at room temperature, and the solution was stirred for overnight at the same temperature, and then methanol was distilled off therefrom under reduced pressure. The remaining aqueous layer was washed with ethyl acetate, and then 1 N hydrochloric acid (52.7 ml.) was added thereto under ice-cooling. The precipitated crystals were collected by filtration, washed with water and then dried to give colorless crystals of 2-(3-methylureido)thiazol-4-ylacetic acid (9.7 g.), mp 190° C. (dec.).

IR Spectrum (Nujol): 3400, 3230, 3100, 1730, 1680 cm$^{-1}$.

(10) 2-Ureidothiazol-4-ylacetic acid (a) To a solution of ethyl 2-aminothiazol-4-ylacetate (1.86 g.) in dried ethyl acetate (37 ml.) was dropwise added trichloromethylisocyanate (1.6 g.) with stirring under ice-cooling. The mixture was stirred for 2 hours at room temperature, and trichloromethylisocyanate (0.32 g.) was further added thereto, and then the mixture was further stirred for 1 hour at room temperature. After the reaction, the reaction mixture was filtered. The filtrate was washed with a saturated aqueous solution of sodium chloride and dried over magnesium sulfate, and then the solvent was distilled off therefrom. The residue was pulverized in diethyl ether to give colorless crystals of ethyl 2-(3-trichloromethylureido)-thiazol-4-ylacetate (1.72 g.).

IR Spectrum (Nujol): 3250, 3150, 1740, 1700 cm$^{-1}$.

(b) A solution of ethyl 2-(3-trichloromethylureido)-thiazol-4-ylacetate (6.32 g.) in a mixture of methanol (400 ml.) and water (150 ml.) was adjusted to pH 7 to 7.6 with sodium bicarbonate aqueous solution with stirring at room temperature, and then the solution was stirred for 70 minutes at the same temperature. The methanol was distilled off from the reaction mixture under reduced pressure, and the precipitates were collected by filtration, washed with water and then dried to give colorless crystals of ethyl 2-ureidothiazol-4-ylacetate (3.45 g.), mp 173° to 174° C.

IR Spectrum (Nujol): 3475, 3150, 1735, 1750, 1680 cm$^{-1}$.

(c) To a solution of ethyl 2-ureidothiazol-4-ylacetate (3.1 g.) in a mixture of methanol (62 ml.) and water (41 ml.) was dropwise added 1 N potassium hydroxide aqueous solution (13.6 ml) with stirring under ice-cooling, and the solution was stirred for overnight at room temperature, and then the solvent was distilled off therefrom. The residue was dissolved in water (150 ml.), washed with ethyl acetate and then adjusted to pH 3.5 with 10% hydrochloric acid. Thus obtained aqueous layer was cooled with ice, and the precipitates were collected by filtration, washed with cold water (10 ml.) and then dried to give colorless crystals of 2-ureido-thiazol-4-ylacetic acid (2.44 g.), mp 189° C. (dec.).

IR Spectrum (Nujol): 3550, 3280, 3050, 1725 cm$^{-1}$.

(11) 2-Amino-4-methylthiazol-4-ylacetic acid hydrobromide

To a mixture of 3-bromo-4-oxovaleric acid (4.0 g.) in ethanol (50 ml.) was added powder of thiourea (1.6 g.) and the mixture was stirred for 3 hours at the room temperature, and then the precipitated crystals were collected by filtration and then dried to give 2-amino-4-methylthiazol-4-ylacetic acid hydrobromide (1.5 g.).

IR Spectrum (Nujol): 1710, 1630, cm$^{-1}$.

What we claim is:

1. The compound 3-(5-methyl-1,3,4-thiadiazol-2-yl)thiomethyl-7-(2-trifluoroacetamidothiazol-4-yl)acetamido-3-cephem-4-carboxylic acid.

2. The compound 3-(1-methyl-1H-tetrazol-5-yl)thiomethyl-7-(2-trifluoroacetamidothiazol-4-yl)acetamido-3-cephem-4-carboxylic acid.

3. The compound 3-(1-methyl-1H-tetrazol-5-yl)thiomethyl-7-(2-methanesulfonamidothiazol-4-yl)acetamido-3-cephem-4-carboxylic acid.

4. The compound 3-(1-methyl-1H-tetrazol-5-yl)thiomethyl-7-(2-benzenesulfonamidothiazol-4-yl)acetamido-3-cephem-4-carboxylic acid.

5. The compound 3-(1-methyl-1H-tetrazol-5-yl)thiomethyl-7-(2-ureidothiazol-4-yl)acetamido-3-cephem-4-carboxylic acid.

6. The compound 3-(1-methyl-1H-tetrazol-5-yl)thiomethyl-7-[2-(3-methylureido)thiazol-4-yl]acetamido-3-cephem-4-carboxylic acid.

7. The compound 3-(1-methyl-1H-tetrazol-5-yl)thiomethyl-7-(2-methanesulfonamidothiazol-5-yl)acetamido-3-cephem-4-carboxylic acid.

8. The compound 3-(1-methyl-1H-tetrazol-5-yl)thiomethyl-7-(2-methanesulfonamidothiazol-5-yl)thioacetamido-3-cephem-4-carboxylic acid.

* * * * *